(12) United States Patent
Ott et al.

(10) Patent No.: US 8,992,590 B2
(45) Date of Patent: Mar. 31, 2015

(54) BIOCOMPATIBILITY LAYER AND COATED OBJECTS

(75) Inventors: Matthias Ott, Dohren (DE); Ingo Grunwald, Bremen (DE); Dirk Salz, Bremen (DE); Michael Wagener, Bremen (DE); Klaus-Dieter Vissing, Thedinghausen (DE); Wolfgang Hielscher, Bremen (DE); Christopher Dölle, Delmenhorst (DE)

(73) Assignees: Fraunhofer-Gesellschaft zur Forderung der Angewandten Forschung E.V., Munich (DE); Bio-Gate AG, Bremen (DE)

( * ) Notice: Subject to any disclaimer, the term of this patent is extended or adjusted under 35 U.S.C. 154(b) by 506 days.

(21) Appl. No.: 13/056,719

(22) PCT Filed: Jul. 31, 2009

(86) PCT No.: PCT/EP2009/059985
§ 371 (c)(1),
(2), (4) Date: Apr. 1, 2011

(87) PCT Pub. No.: WO2010/012836
PCT Pub. Date: Feb. 4, 2010

(65) Prior Publication Data
US 2011/0189493 A1    Aug. 4, 2011

(30) Foreign Application Priority Data
Jul. 31, 2008  (EP) .................................. 08161598

(51) Int. Cl.
| A61F 2/06 | (2013.01) |
| C23C 16/56 | (2006.01) |
| A61L 27/34 | (2006.01) |
| A61L 29/08 | (2006.01) |
| A61L 31/10 | (2006.01) |
| B05D 1/00 | (2006.01) |
| C23C 16/30 | (2006.01) |

(52) U.S. Cl.
CPC ................. *C23C 16/56* (2013.01); *A61L 27/34* (2013.01); *A61L 29/085* (2013.01); *A61L 31/10* (2013.01); *B05D 1/62* (2013.01); *C23C 16/30* (2013.01)
USPC ............................................ 623/1.1; 428/446

(58) Field of Classification Search
USPC ............................................ 623/1.1; 428/446
See application file for complete search history.

(56) References Cited

U.S. PATENT DOCUMENTS

| 4,508,606 A | 4/1985 | Andrade et al. |
| 2005/0018310 A1* | 1/2005 | Kornfield et al. ............. 359/642 |

FOREIGN PATENT DOCUMENTS

| DE | 10 2006 018 491 | 10/2007 |
| WO | WO 2008/074388 | 6/2008 |

\* cited by examiner

*Primary Examiner* — Thomas J Sweet
*Assistant Examiner* — Matthew Schall
(74) *Attorney, Agent, or Firm* — Preti Flaherty Beliveau & Pachios LLP

(57) ABSTRACT

The present invention relates to the use of a crosslinked, silicon-containing layer containing, substantially consisting of or consisting of silicon, O, C, H, optionally N which can be produced by plasma polymerization and/or crosslinking of organosilicon liquids by a plasma process and/or UV radiation of a wavelength of less than 250 nm, without using metals of an atomic number of more than 14, as a biocompatible surface, for imparting to a surface or providing a surface with a non-genotoxic effect. The invention also relates to correspondingly coated articles and to processes for the production thereof.

15 Claims, 17 Drawing Sheets

Figure 1:
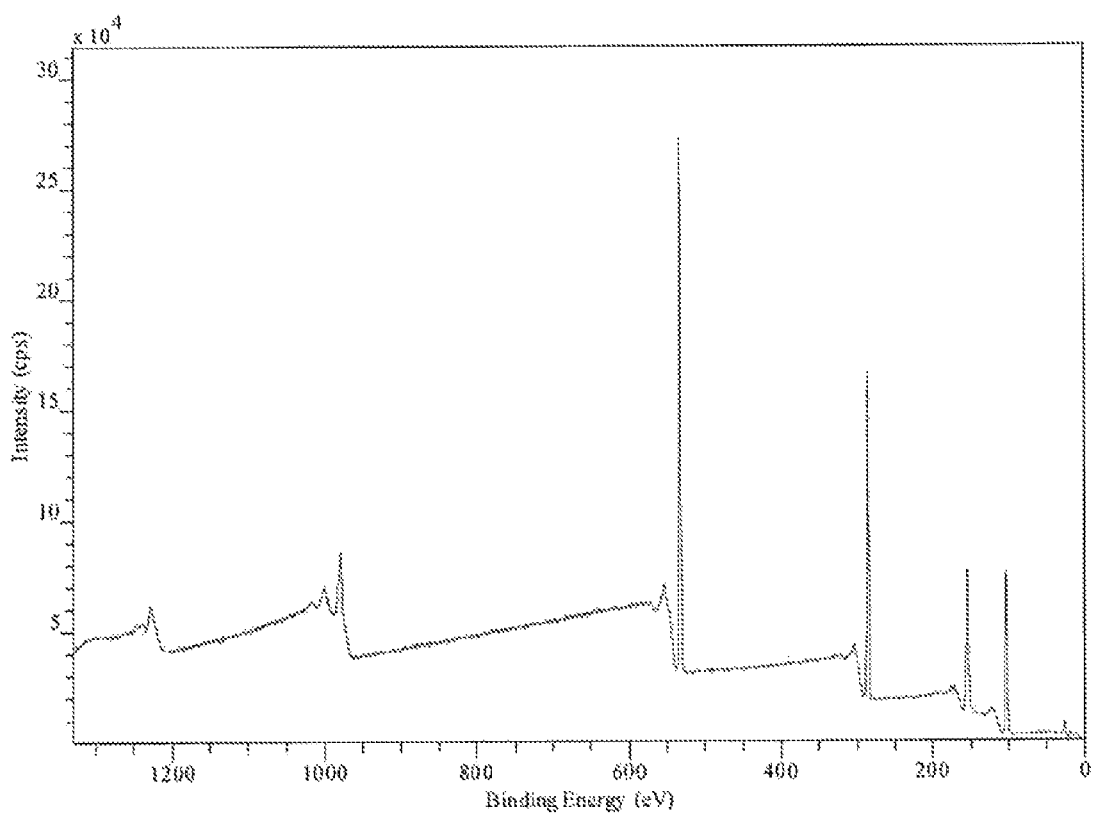

I.  II.

BIOCOMPATIBILITY LAYER AND COATED OBJECTS

The present invention relates to the use of a cross-linked, silicon-containing layer containing, substantially consisting of or consisting of silicon, O, C, H, optionally N which can be produced by plasma polymerization and/or cross-linking of organosilicon liquids by a plasma process and/or UV radiation of a wavelength of less than 250 nm, without the use of metals of an atomic number of more than 14, as a non-genotoxic surface or for imparting to a surface or providing a surface with a non-genotoxic effect. The invention also relates to the use of the layers described above for the defined i) improvement or ii) reduction of the adhesion of biomolecules and/or cells (prokaryotes or eukaryotes). Furthermore, the invention relates to correspondingly coated articles and to processes for the production thereof.

Non-genotoxicity in the context of the present invention generally denotes the characteristic of a material of not exerting genotoxicity or exerting merely an acceptable genotoxicity, measured according to ISO 10993-3:2003. In this respect, the presence of the "non-genotoxicity" characteristic is preferably determined according to the process identified in ISO 10993-3:2003. Alternatively (or in addition), the process described later on in Example 5 of this application is also capable of demonstrating the presence of non-genotoxicity in the context of the present application "in accordance with DIN IN ISO 10993-3".

The characteristic of articles of being non-genotoxic is a particularly challenging requirement, especially in the field of medicine. Genotoxicity exhibits its effect to some extent only after a long period of time. The smallest amounts of a genotoxic substance, if it remains in the body for a relatively long time, can have long-term and possibly fatal effects for an organism. In the field of medicine, depending on the use, non-genotoxicity is not always a prerequisite for adequate biocompatibility, since biocompatibility also includes a biotolerance for specific periods of time which can be shorter than the effective periods of a potentially genotoxic substance.

Thus, a non-genotoxic layer in the context of the present invention is a layer which, when it is in direct contact with living cells, tissue, organs or living beings, in particular a human being or a human cell, tissue or organ, exhibits non-genotoxicity according to the definition described above. According to the invention, non-genotoxic layers preferably form surfaces on articles which are brought into contact with human cells, tissue or organs during intended use, the surface of the article which is in contact with the cells, tissue or organs being at least partially covered with a non-genotoxic layer. Articles which are brought into contact with human cells, tissue or organs during intended use are also simply termed medical products in the context of this invention.

Various articles with a biocompatible (and to some extent also a non-genotoxic) surface are already known as such. However, as stated in the following, up until now it has been laborious to produce corresponding surfaces on these articles, or to transfer processes which lead to the formation of such a surface for a specific article, to other articles.

In various technical fields, such as sensor technology, but particularly also in the field of medical products, for example in the case of implants, stents, pacemakers, injection systems or catheters, the compatibility of the materials used plays an important part. In addition to the general good compatibility of such articles, additional characteristics are almost always required in the respective fields of application. To achieve these characteristics, the surfaces of the articles are conventionally treated by (wet) chemical and/or physical processes. The purpose of this is, for example, for proteins such as albumin and fibronectin to adhere more effectively to the treated surfaces. An example of such a surface treatment is the application of suitable surface groups, for example amino, hydroxyl or carboxyl groups. The objective here is for the respectively treated articles (for example implants) to be able to adapt more easily to tissue structures which are present, in that for example in the case of implants, they are joined more firmly to bone tissue and this attachment turns out to be relatively compatible, particularly in that local pathological effects in local tissue are restricted or reduced to a macroscopic and microscopic level. In other cases as well, the purpose of a surface treatment is for (body) cells, in particular bone cells, tissue cells, endothelial cells to become attached to these surfaces and to grow thereover, so that the article, for example the implant integrates more quickly into the surrounding tissue. On the one hand, this is desirable for an improved anchorage and compatibility. On the other hand, this accelerates the healing process and reduces the risk of inflammation and rejection.

However, attempts are made to achieve precisely the opposite effect for some articles, that is, to prevent the attachment of biomolecules and cells to specific surfaces. An attachment can result in an undesirable restriction of operation, for example in the field of sensors, but also in the blocking of cannulas or tubes. These effects are also termed fouling. Implants often have zones where cell growth is undesirable. In the case of short-term catheters, a tissue integration which is too successful can complicate the simple removal of said catheters.

A further disadvantageous effect of surfaces which can be effectively joined to biomolecules and cells is that an undesirable interaction between cells and the introduced materials can induce cell-biological reactions, such as inflammation reactions and cell agglomerations which can result in extremely serious side effects.

The settlement of implant surfaces or prostheses by microorganisms, for example by antibiotic-resistant Staphylococci, is a serious problem in medicine. The infection of patients, respectively the colonization of the implants can result in life-threatening side effects. These can often only be overcome by a very expensive implant replacement and by a long stay in hospital. Bacterial adhesion is always preceded by an adhesion of biomolecules such as proteins from the serum. Suitable anti-adhesive coatings can significantly reduce the colonization by bacteria.

To treat illnesses, for example infections, infusions are frequently given or venous punctures are made. In so doing, the patient is usually fitted with a catheter, or a port or a cannula is inserted. In the passage region, or in the body, inflammatory reactions often develop which are caused, inter alia by the inserted material. A coating which promotes the cell adhesion can reduce these undesirable reactions.

For the treatment of very serious diseases, for example aggressive tumors, autoimmune diseases or infections, new protein- and DNA-based medicaments have been available for some years. These are, for example antibodies against tumor cells, peptide antibiotics against infections or siRNA against autoimmune diseases. The advantage of these new active substances is, inter alia, that they are effective in relatively small quantities. However, the problem arises here that during administration (for example intravenously), these substances adsorb on the surfaces of the syringes, tubes or storage bottles, thus become unspecifically and undesirably attached. To compensate for the loss of active substance, they are usually administered in a 15-25% higher dose than is actually required.

A further objective of the coating is to allow a non-damaging interaction between a hollow fiber of membrane oxygenators and blood. An oxygenator is part of a heart and lung machine which supplies oxygen to the blood. The oxygenator comprises hollow fibers through which oxygen is conducted. The blood flow passes along the outer surface of the fibers. This so-called membrane oxygenator exchanges carbon dioxide for oxygen.

Numerous attempts have routinely been made to provide surfaces with fouling-inhibiting or fouling-delaying characteristics (so-called "anti-fouling surfaces") and/or with anti-adhesive characteristics. Some of these attempts will be briefly described in the following. In so doing, those documents are also acknowledged, whose content has only retrospectively been recognized as being structurally at least slightly similar, i.e. with knowledge of the finished present invention, even if they do not contain any suggestions for achieving the object of the invention.

According to the prior art, implant surfaces for example can be coated with polyethylene glycol (PEG), poly(ethylene oxide) (PEO) or similar polymers by wet chemical processes to produce anti-fouling or anti-adhesive coatings.

It is known that surfaces can be coated with $CHF_3$-pulse plasmas such that it is possible to influence the adhesion and the growth of cells (M. Haupt, J. Barz, U. Vohrer, H. Hilgers, C. Oehr in Vakuum in Forschung and Praxis, 2005, Vol. 17, $6^{th}$ Edition, pages 329-335). However, such a procedure is associated with the problems known from using fluorine-containing plasmas: the precursors are relatively expensive and can lead to carcinogenic intermediate products.

Furthermore, the deposition of special silicon carbide plasma coatings for improving the bio- and hemocompatibility of stent basic bodies is known (presentation by Dr. Carsten Momma on the range of topics "Plasma technology in vessel medicine" on the innovation forum "Plasma Plus Bio" on 2 Feb. 2006 in Greifswald). This is a very expensive coating process, since the coating installations have to be equipped for high vacuum.

U.S. Pat. No. 5,182,317 discloses a coating process in which a surface coating is functionalized with amines. The process is relatively complex and correspondingly expensive to carry out. Similarly complex processes are known, for example from U.S. Pat. No. 5,455,040.

In membrane oxygenators, at the present time heparin molecules are often bound to the outer surface of the fibers for example by a chemical process. However, this method suffers from the disadvantage that it is very complex and the oxygen/carbon dioxide exchange in the blood with thus treated fibers does not function effectively.

Furthermore, DE69932273 T2 discloses that oxygenator fibers can be provided with amine functionalities. This is carried out by applying an amine-functional polysiloxane solution. The thus functionalized surface is then brought into contact with a biomolecule, for example with heparin. Heparin is to prevent the formation of thrombi, so that the risk of thrombosis for the patient is reduced. Commercially, oxygenators with this coating are sold under the brand name "QUADROX Bioline coated".

Alternatively, the surface of the oxygenator fibers is made to be biocompatible by means of polypeptides. These are sold under the trade name "QUADROX Safeline treated".

U.S. Pat. No. 6,549,811 discloses the use of plasma polymeric coatings for structuring the surfaces of elastomers such as silicone catheters.

EP1060031B1 describes the crosslinking of silicone oil with plasma as a coating for a container for a pharmaceutical protein preparation. The coating is to reduce the adhesion of proteins to the coated surface.

WO 2005/014075 A1 generally discloses a plasma polymerization with siloxanes for coating "expansion balloons" to improve abrasion resistance and to prevent very small holes.

EP1701676B1 discloses a wound dressing which has an antimicrobially effective substance (silver) in a polymer formed from hexamethyldisiloxane by plasma polymerization. No information is provided about an anti-fouling effect or anti-adhesive characteristics of a silver-free surface.

DE 103 537 56 discloses an antimicrobial, non-cytotoxic layer material. The layer material contains silver and a plasma polymeric layer as the transport control layer. However, this document does not disclose that cytotoxicity can also be prevented without any silver being present or even non-genotoxicity can be produced within the meaning of the invention. Furthermore, the described process does not allow the coating of complex component shapes, or only when a considerable amount of effort is involved.

Likewise, U.S. Pat. No. 6,589,546 generally discloses an active substance release system with a plasma polymeric cover layer, but without a detailed explanation about interactions with body cells.

WO 02100928 A1 discloses various plasma polymeric layers, but without giving an indication of possible interactions with body cells or the use in direct contact with body tissue.

Known from EP 982041 A1 are special plasma coatings with functionalized siloxanes. They are to be used to form thrombus-resistant coatings for medical instruments. The presented coatings are expensive to produce.

DE 10031198 A1 very generally discloses plasma coatings of medical surfaces. The coatings are to act as a protection against corrosion. Nothing specific is stated about an improved biocompatibility.

Furthermore, EP 745220 B1 discloses "bio-inert" solid phase sensors with a coating formed from silicone carbinol.

DE 10 2006 018 491 A1 discloses plasma polymeric layers of a specific composition which are described quite generally as "non-cytotoxic" or "improving body compatibility". Furthermore, this document discloses that these layers can be provided on medical articles which can be implanted. However, this is not an indication of the presence of, or the allowing of a non-genotoxicity in the context of the present application. On the one hand, the type of articles which can be implanted is not specified, so that it is unclear whether they are only to be implanted for a short time in the body or are to remain there for very long periods of time. On the other hand, only an improvement in the body compatibility is discussed in the corresponding document in connection with medical articles which can be implanted in the sense of reducing the adhesion of bacteria, proteins or other substances produced naturally in the body, but this likewise does not contain any indication of the presence of non-genotoxicity.

It was therefore the object of the present invention to remedy the disadvantages of the prior art or to reduce these disadvantages and to specify improved coatings and correspondingly coated articles and uses of the coatings. In particular, possibilities should be presented to a person skilled in the art to provide medical articles with surface characteristics in an economical and effective manner, which surface characteristics are advantageous for use relating to contact with parts of the body. In this connection, it should be particularly noted that even long-term periods of contact do not give rise to a damaging effect in the body even over a long period of time. Such long-term periods of contact can ensue, for example due to a permanent implant or by abraded remnants (even in very small quantities) which are even produced during only temporary (short-term) contact with the body and in an unfavorable case can remain in permanent contact therewith (in that they are incorporated for example).

The object is achieved by specifying a use of a crosslinked silicon-containing layer containing, substantially consisting of or consisting of silicon, O, C, H, optionally N which can be produced by plasma polymerization and/or crosslinking of organosilicon liquids by a plasma process and/or UV radiation of a wavelength of less than 250 nm, without using metals of an atomic number of more than 14, having an atomic ratio of oxygen to silicon of 0.75 to 2.2 and an atomic ratio of carbon to silicon of 0.1 to 2.5, measured by XPS, as a non-genotoxic surface or for imparting to a surface or providing a surface with a non-genotoxic effect.

In particular, a non-genotoxic effect is imparted or modified according to the invention by influencing in a defined manner the chemical composition of the surface of the silicon-containing layer. In this way, the adhesion of biomolecules and/or pro- and/or eukaryotic cells can also be adjusted in a defined manner (cf. further below as well).

The term "non-genotoxic layer" in the context of the invention is therefore understood as meaning in particular a silicon-containing layer, containing, substantially consisting of or consisting of silicon, O, C, H, optionally N which can be produced by plasma polymerization and/or crosslinking of organosilicon liquids by a plasma process and/or UV radiation of a wavelength of less than 250 nm, without using metals of an atomic number of more than 14.

The use of a non-genotoxic layer according to the invention makes it possible in particular to ensure the non-genotoxicity of a correspondingly coated article, as described at the outset. Non-genotoxic layers to be used according to the invention are easy to produce, the production costs can be kept down by using suitable precursors, the non-genotoxic layers can be produced to be very thin yet fully effective and the adhesion of cells, proteins, nucleic acids and fatty acids can be easily adjusted. The production of corresponding layers can be carried out as a pure gas phase process under vacuum, so that the risk of the release of unreacted monomers can be practically completely avoided. As described in the following, layers to be used according to the invention can be applied to a large number of different solid substrates, and it is also possible for surfaces of complicated shapes to be provided uniformly with the non-genotoxic layer. These and other advantages of the non-genotoxic layer to be used according to the invention and of correspondingly coated articles will be set out in more detail in the following.

Due to the use according to the invention, it is possible in a reproducible manner and with surprisingly little effort to provide a uniform material for imparting non-genotoxic characteristics to a large number of articles and surface base materials and for the most varied areas of application. In this respect, achieving non-genotoxicity in the context of the present application is a surprising effect. During the production processes for the layer to be used according to the invention, a large number of very reactive species (radicals, charged particles, in each case of a different size which cannot in principle be precisely defined) are always produced. Such reactive species are always potential initiators of genotoxicity. For this reason, it was not possible to predict the effect that the layers to be used according to the invention satisfy the requirement of a lack of genotoxicity.

In addition to imparting non-genotoxic characteristics, the use according to the invention preferably makes it possible to provide an article with a surface which has, with respect to humans and their organs no cytotoxicity or merely an acceptable cytotoxicity, measured according to ISO 10993-5:2003, in particular according to point 8.3 of ISO 10993-5:2003, the cultures being incubated in a culture medium with 10% fetal calf serum at 37° C. (±2° C.) at 5% v/v carbon dioxide, no irritation or merely an acceptable irritation or intracutaneous reactivity, measured according to ISO 10993-10:2003, no systemic toxicity or merely an acceptable systemic toxicity (acute toxicity, subacute toxicity and subchronic toxicity, measured according to ISO 10993-11:2003, satisfactory or good implantation compatibility, measured according to ISO 10993-6:2003, and/or satisfactory or good hemocompatibility, measured according to ISO 10993-4:2003, and depending on the field of use of an article coated according to the invention, one or more of the mentioned characteristics can be achieved, in addition to non-genotoxicity of the article; more on this below.

Preferred according to the invention is a use in which the layer to be used according to the invention is also used for a defined (i) improvement or (ii) reduction in the adhesion of biomolecules and/or cells (pro- or eukaryotes).

Thus, a further aspect of the invention is the use of a crosslinked silicon-containing layer containing, substantially consisting of or consisting of silicon, O, C, H, optionally N which can be produced by plasma polymerization and/or crosslinking of organosilicon liquids by a plasma process and/or UV radiation of a wavelength of less than 250 nm, without using metals of an atomic number of more than 14, having an atomic ratio of oxygen to silicon of 0.75 to 2.2 and an atomic ratio of carbon to silicon of 0.1 to 2.5, measured by XPS, for the defined (i) improvement or (ii) reduction in the adhesion of biomolecules and/or cells (pro- or eukaryotes)

or the previously described use preferred according to the invention, in each case provided that in case the adhesion is reduced by the use, the layer is not a layer consisting of carbon, silicon, oxygen and hydrogen and optionally usual impurities, and in the ESCA spectrum of the layer, upon calibration on the aliphatic portion of the C 1s peak at 285.00 eV, compared to a trimethylsiloxy-terminated polydimethylsiloxane (PDMS) with a kinematic viscosity of 350 mm$^2$/s at 25° C. and a density of 0.97 g/mL at 25° C., the Si 2p peak has a bond energy value which is shifted by at most 0.45 eV to higher or lower bond energies, and the O 1s peak has a bond energy value which is shifted by at most 0.50 eV to higher or lower bond energies.

In this respect, it can be preferred according to the invention that furthermore layers are excluded, i.e. also in particular come under the above provision, for which the Si 2p peak has a bond energy value which is shifted by at most 0.45 eV to lower bond energies and/or the O 1s peak has a bond energy peak which is shifted by at most 0.70 eV to higher or lower bond energies.

As already described above, with this aspect of the invention, it is possible to increase or decrease the adhesion for specific biomolecules and/or cells by a desired amount.

The layers which are excluded above for the use according to the invention are disadvantageous, because the production thereof requires a high expense in terms of apparatus. The reason for this is that, for the coating process, a relatively very low moisture for low-pressure plasma processes is allowed in the process gas. Thus, it is stated in DE 10 2006 018 491 A1 that for the production of these layers, the leakage rate of the vacuum chamber used is significantly less than $2 \times 10^{-9}$ mbar L per second. This implies higher investment costs, since a higher demand is made on the plasma installation in respect of tightness. Furthermore, it is immediately apparent to a person skilled in the art from the examples described in the mentioned document that a significantly longer pump-out time is required which can result in the duration of the process being prolonged. Since only in this manner is it possible in a low-pressure pilot plant which, like conventional production plants has walls made of stainless steel and cannot be fully heated, for the measured value of the mass 18 (water) to fall markedly and then remain constant with a high sensitivity of the spectrometer. In this case, pump-out times of approximately one hour are usual here. However, since the pumping-out procedure generates almost the same costs as the coating procedure itself, a prolongation of the processing time also implies a corresponding increase in the coating costs. It is demonstrated in Example 1 (cf. further below) that in the case of the layer produced there, plasma polymer A6, only a short pump-out time is possible.

A non-genotoxic article is also specified according to the invention which comprises a surface region with a crosslinked silicon-containing layer containing, substantially consisting of or consisting of silicon, O, C, H, optionally N which can be produced by plasma polymerization and/or crosslinking of organosilicon liquids by a plasma process and/or UV radiation of a wavelength of less than 250 nm, without using metals of an atomic number of more than 14, having an atomic ratio of oxygen to silicon of 0.75 to 2.2 and an atomic ratio of carbon to silicon of 0.1 to 2.5, measured by XPS, the article being selected from the group consisting of:
a) membrane, pipe and tube, in particular oxygenator membrane, catheter, angioplasty balloon, stent, cannula, sensor and probe,
b) an article implanted for an intended use, selected from the group consisting of: medical nails, clasps, threads and screws, in particular bone attachment nails, stents or vessel prostheses, injection systems, catheters, cardiovascular implants, artificial organs, in particular pacemakers and a power source thereof, prostheses, orthopedic implants, in particular artificial joint mouse, in particular a socket and a counterpart cooperating therewith such as a hip or knee prosthesis, spine prosthesis, cochlea implants, artificial heart valves, heart valve rings or intraocular lenses, artificial corneas, pumps or other devices for releasing substances in the body and epitheses,
c) a container for receiving and/or transporting bodily fluid, tissue or the constituents thereof of a living being or of biomolecules, preferably peptides, proteins, lipids, carbohydrates, nucleic acids or active substances prepared therewith,
d) an article for the at least partial covering of skin or mucous membrane of a living being and preferably of wounds,
e) an article otherwise in contact with bodily fluid, tissue or the constituents thereof of a living being or with biomolecules, preferably peptides, proteins, lipids, carbohydrates, nucleic acids or active substances prepared therewith during intended use.

Non-genotoxic layers to be used according to the invention are used according to the invention to adjust defined conditions in respect of growth of body cells and/or genotoxicity on articles particularly of medical technology. In this respect, both a good and a reduced growth can be realized, the respective coatings displaying a non-genotoxic function in both fields of application. In parallel with the growth behavior of body cells, it is possible for the bacterial adhesion on the coated surfaces to be reduced. It could be shown here that there are organosilicon coatings to be used according to the invention for which the adhesion of gram-negative and also at the same time gram-positive bacteria is greatly reduced. Blood compatibility tests show that no coagulation occurs.

An article, around which or through which flows bodily fluid of a living being or one of its constituents during intended use in the context of the invention, is preferably a membrane, a pipe or tube, in particular an oxygenator membrane, a catheter, an angioplasty balloon, a stent or a cannula.

An article implanted during intended use in the context of the invention is preferably an implant, a medical nail, a clasp, a thread and/or a screw, in particular a bone attachment nail, a stent, a cannula, a sensor and a probe or a vessel prosthesis, an injection system, a catheter, a cardiovascular implant, an artificial organ, in particular a pacemaker and a power source thereof, a prosthesis, an orthopedic implant, in particular an artificial joint mouse, in particular a socket and a counterpart cooperating therewith such as a hip or knee prosthesis, a spine prosthesis, a cochlea implant, a dental implant, an artificial heart valve, a heart valve ring, an intraocular lens, an artificial cornea, a pump or another device for releasing substances in the body and epitheses.

A container for receiving and/or transporting bodily fluid, tissue or the constituents thereof of a living being or of biomolecules, preferably peptides, proteins, lipids, nucleic acids or active substances prepared therewith in the context of the invention is preferably a dish, a blood-preserving pouch, a cell culture container, a fermenter.

An article for the at least partial covering of skin or mucous membrane of a living being and preferably of wounds in the context of the invention is preferably a wound dressing, a bandage, a plaster, a contact lens, an incontinence product.

An article otherwise in contact with bodily fluid, tissue or the constituents thereof of a living being or with biomolecules, preferably peptides, proteins, nucleic acids or active substances prepared therewith during intended use in the context of the invention is preferably:
  a sensor in particular for in-vivo analysis or for ex-vivo analysis, preferably a sensor for examining bodily fluid, in particular blood, serum and lymph, body cells, tissue, organ(s),
  a probe for insertion in a human or animal body, preferably a stomach probe, an endoscope, a probe for measuring intracranial pressure,
  a pump or another device for releasing substances in the body,
  a medicament container, in particular with contents containing peptides, proteins, fatty acids and/or nucleic acids, in particular liposomes and/or DNA-based active substances or transport vehicles,
  part of a bioreactor on which biocatalysts, for example enzymes or microorganisms are fixed,
  a filter material for filtering cells and/or biologically producible macromolecules out of a liquid.

A layer to be used according to the invention is preferably wipe-resistant on the substrate. As used herein, the term "wipe-resistant" means resistant to a one-off manual wiping with isopropanol-impregnated, two-ply cosmetic and all-purpose wipes made of soft tissue (produced for example by TEMCA GmbH). The layers to be used according to the invention also preferably have a modulus of elasticity of more than 0.5 GPa or a hardness of more than 0.05 GPa, more preferably a modulus of elasticity of more than 0.8 GPa or a hardness of more than 0.07 GPa, in each case measured by means of nano-identification. The determining measuring method in case of doubt is described in WO 2009/056635 A2, Example 2, which becomes part of this text by way of reference.

Furthermore, it is preferable to produce a layer to be used according to the invention or an article according to the invention (during coating) in the presence of oxygen-containing gases which do not contain carbon or silicon (even respectively in compounds). Such gases are then additionally added to possible gaseous precursors or fragments of the precursors during the production of the layer. Preferred examples of such gases are $O_2$, $N_2O$ and $H_2O$.

Often preferred on the one hand is an article according to the invention, the non-genotoxic surface of which has in the region of the layer to be used according to the invention an atomic ratio of oxygen to silicon of 1.6 to 2.2, an atomic ratio of carbon to silicon of 0.1 to 0.5 and an atomic ratio of carbon to oxygen of 0.01 to 0.2. Such layers are in particular hemocompatible and thus particularly suitable as a coating for oxygenator membranes and other surfaces which come into contact with blood, in particular surfaces of implants. Such layers preferably have a water contact angle of not more than 35°, preferably not more than 25° and more preferably from 0 to 15°.

On the other hand, often preferred is also an article according to the invention, the non-genotoxic surface of which has in the region of the layer to be used according to the invention an atomic ratio of oxygen to silicon of 0.75 to 2.0, an atomic ratio of carbon to silicon of 0.6 to 2.5 and an atomic ratio of carbon to oxygen of 0.4 to 3.0 and an atomic ratio of hydrogen to carbon of 1.5 to 3.2.

The adhesion tendency of biological materials, in particular of bacteria, fungi and eukaryotic cells to thus coated articles is greatly reduced compared to metal surfaces, such as titanium surfaces. Therefore, these surfaces are particularly suitable for articles according to the invention which are to remain free from the growth or attachment of biological materials, such as cannulas and medicament containers. In the following, this non-genotoxic layer is to be called "biocompatibility layer A".

The following substance ratios apply particularly preferably to biocompatibility layer A of these articles:
$0.85 < n(O):n(Si) < 1.8$
$0.8 < n(C):n(Si) < 2.8$
$0.5 < n(C):n(O) < 2.6$
$1.8 < n(H):n(C) < 3.1$.

The following applies most particularly preferably to biocompatibility layer A of these articles:
$1.0 < n(O):n(Si) < 1.7$
$1.4 < n(C):n(Si) < 2.6$
$0.9 < n(C):n(O) < 2.4$
$2.2 < n(H):n(C) < 3.0$.

In this respect, the substance ratios of all pairs of atoms without hydrogen relate to XPS measurements with adjustments which produce substance ratios of $n(O):n(Si)=1.02$, $n(C):n(Si)=2.35$ and $n(C):n(O)=2.29$ for a trimethylsiloxy-terminated polydimethylsiloxane (PDMS), used as standard, with a kinematic viscosity of 350 $mm^2/s$ at 25° C. and a density of 0.97 g/mL at 25° C. The ratio between hydrogen and carbon relates to results of the conventional chemical ultimate analysis.

In respect of the substance proportions of elements silicon, oxygen and carbon, it preferably applies that biocompatibility layer A of these articles, based on 100 atom % for the total of the elements silicon, oxygen and carbon, contains:
Silicon: 18 to 30 atom %
Oxygen: 20 to 50 atom %
Carbon: 25 to 60 atom %.

However, it is particularly preferred when the biocompatibility layer A of these articles, based on 100 atom % for the total of the elements silicon, oxygen and carbon, contains:
Silicon: 20 to 28 atom %
Oxygen: 22 to 45 atom %
Carbon: 35 to 55 atom %.

In this respect, the atom % values relate to XPS measurements for adjustments which produce for silicon 22.9 atom %, for oxygen 23.4 atom % and for carbon 53.75 atom % for a trimethylsiloxy-terminated polydimethylsiloxane (PDMS), again used as standard, with a kinematic viscosity of 350 $mm^2/s$ at 25° C. and a density of 0.97 g/mL at 25° C.

While bearing in mind preferred weight proportions and substance ratios, biocompatibility layer A of these articles is particularly preferred when it contains, based on 100 atom % for the total of the elements silicon, oxygen and carbon:
Silicon: 18 to 30 atom %
Oxygen: 20 to 50 atom %
Carbon: 25 to 60 atom %,
where the following applies to the substance ratios in biocompatibility layer A of these articles:
$0.75 < n(O):n(Si) < 2.0$
$0.6 < n(C):n(Si) < 3.0$
$0.4 < n(C):n(O) < 3.0$
$1.5 < n(H):n(C) < 3.2$ and
where in the XPS spectrum of the biocompatibility layer of these articles, compared to a trimethylsiloxy-terminated polydimethylsiloxane (PDMS), with a kinematic viscosity of 350 $mm^2/s$ at 25° C. and a density of 0.97 g/mL at 25° C., the Si 2p peak has a bond energy value which is shifted by at most 0.8 eV to higher or lower bond energies and the O 1s peak has a bond energy value which is shifted by at most 0.7 eV to higher or lower bond energies.

The statements made above in respect of the XPS measurements and the selected standard apply here accordingly.

A most particularly preferred biocompatibility layer A of these articles contains, based on 100 atom % for the total of the elements silicon, oxygen and carbon:
Silicon: 20 to 28 atom %
Oxygen: 22 to 32 atom %
Carbon: 38 to 53 atom %
where the following applies to the substance ratios of biocompatibility layer A of these articles:
$1.0 < n(O):n(Si) < 1.7$
$1.4 < n(C):n(Si) < 2.6$
$0.9 < n(C):n(O) < 2.4$
$2.2 < n(H):n(C) < 3.0$ and
where in the mentioned ESCA spectrum, the Si 2p peak has a bond energy value which is shifted by at most 0.60 eV to higher or lower bond energies and the O 1s peak has a bond energy value which is shifted by at most 0.65 eV to higher or lower bond energies.

In this respect, in preferred practical examples, the layers excluded from a use according to the invention for reducing the adhesion can also be excluded from the non-genotoxic articles according to the invention.

Likewise preferred is a biocompatibility layer A which has a proportion of 0.1 to ≤5% of carbon atoms with a bond to precisely two oxygen atoms ("COO"), measured by XPS. Accordingly, a maximum of 5% of the carbon atoms of the silicon-containing layer are present as ester or acid groups. More preferred is a proportion of ≤3%.

Also preferred is a biocompatibility layer A which has a proportion of ≤12% of carbon atoms with a bond to precisely one oxygen atom ("C—O"), measured by XPS. Accordingly, a maximum of 12% of the carbon atoms of the silicon-containing layer are present as hydroxyl or ether groups. More preferred is a proportion of ≤8%.

This effectively reduces the adhesion of biomolecules.

The proportion of carbon atoms with a bond to precisely one oxygen atom ("C—O") and to precisely two oxygen atoms ("COO") is determined in that the XPS spectra which have been measured oriented to the sample standard are subjected to a curve fitting. Assuming that the nitrogen concentration in the coating is low (<0.5 atom %), the chemical shifts are interpreted at the C1s spectrum, as stated in Table 1:

| Abbreviation | Peak number (in FIG. 3-8) | Groups | Bond energy |
|---|---|---|---|
| "C" | I | Aliphatic | 285.0 eV |
| "C—O" | II | Alcohol, Ether | 286.5 ± 0.2 eV |
| "COO" | III | Carboxyl, Ester | 289.2 ± 0.2 eV |

For biocompatibility layer A according to the invention, it can occasionally be preferred for the contact angle on a planar surface at 25° C. to be a water contact angle of at least 90°, preferably at least 95° and more preferably at least 100°.

Particularly preferred is an article according to the invention with a non-genotoxic layer which consists to more than 98% of the elements silicon, carbon, oxygen, hydrogen and nitrogen. Further preferred is an article according to the invention with a non-genotoxic layer which consists to more than 98% of the elements silicon, carbon, oxygen and hydrogen. As described further in the following, such layers can be produced in a particularly effective manner for realizing the above-mentioned advantages.

Non-genotoxic layers for applications which require particularly hydrophilic and hemocompatible surfaces are designated in the following as biocompatibility layers B. In this specific practical example of the invention, the carbon atoms of biocompatibility layer B preferably have a proportion of 5-35% of carbon atoms with a bond to precisely one oxygen atom ("C—O"), measured by XPS. Accordingly, 5-35% of the carbon atoms of the silicon-containing layer are present as hydroxyl or ether groups. More preferred is a proportion of 10-30%, preferably 15-25%. Particularly hydrophilic and hemocompatible layers can be produced in this manner. In particular, these preferred bond variants have the advantage that the adhesion of biomolecules, particularly preferably albumin and fibromectin, is improved, as a result of which the cell growth is also improved.

The following substance ratios apply particularly preferably to biocompatibility layer B of these articles:
1.8<n(O):n(Si)<3.0
0.1<n(C):n(Si)<1.2
0.05<n(C):n(O)<0.6
0.5<n(H):n(C)<3.0.

The following applies most particularly preferably to biocompatibility layer B of these articles:
2.2<n(O):n(Si)<2.5
0.2<n(C):n(Si)<0.7
0.05<n(C):n(O)<0.4
1.0<n(H):n(C)<2.2.

In this respect, the substance ratios of all pairs of atoms without hydrogen relate to XPS measurements with adjustments which produce substance ratios of n(O):n(Si)=1.02, n(C):n(Si)=2.35 and n(C):n(O)=2.29 for a trimethylsiloxy-terminated polydimethylsiloxane (PDMS), used as standard, with a kinematic viscosity of 350 mm$^2$/s at 25° C. and a density of 0.97 g/mL at 25° C. The ratio between hydrogen and carbon relates to results of the conventional chemical ultimate analysis.

In respect of the substance proportions of the elements silicon, oxygen and carbon, it preferably applies that biocompatibility layer B of these articles, based on 100 atom % for the total of the elements silicon, oxygen and carbon, contains:
Silicon: 18 to 32 atom %
Oxygen: 45 to 70 atom %
Carbon: 3 to 25 atom %.

However, it is particularly preferred when biocompatibility layer B of these articles, based on 100 atom % for the total of the elements silicon, oxygen and carbon, contains:
Silicon: 24 to 30 atom %
Oxygen: 50 to 68 atom %
Carbon: 3 to 19 atom %.

In this respect, the atom % values relate to XPS measurements for adjustments which produce for silicon 22.9 atom %, for oxygen 23.4 atom % and for carbon 53.75 atom % for a trimethylsiloxy-terminated polydimethylsiloxane (PDMS), again used as standard, with a kinematic viscosity of 350 mm$^2$/s at 25° C. and a density of 0.97 g/mL at 25° C.

While bearing in mind preferred weight proportions and substance ratios, biocompatibility layer B of these articles is particularly preferred when it contains, based on 100 atom % for the total of the elements silicon, oxygen and carbon:
Silicon: 18 to 32 atom %
Oxygen: 45 to 70 atom %
Carbon: 3 to 25 atom % and
where the following applies to the substance ratios in biocompatibility layer B of these articles:
1.8<n(O):n(Si)<3.0
0.1<n(C):n(Si)<1.2
0.05<n(C):n(O)<0.6
0.5<n(H):n(C)<3.0.

The statements made above in respect of the XPS measurements and the selected standard apply here accordingly.

A most particularly preferred biocompatibility layer B of these articles contains, based on 100 atom % for the total of the elements silicon, oxygen and carbon:
Silicon: 24 to 30 atom %
Oxygen: 50 to 68 atom %
Carbon: 3 to 19 atom %
where the following applies to the substance ratios of biocompatibility layer B of these articles:
2.2<n(O):n(Si)<2.5
0.2<n(C):n(Si)<0.7
0.05<n(C):n(O)<0.4
1.0<n(H):n(C)<2.2.

Furthermore, biocompatibility layer B according to the invention of these articles, during measurement with a progressing contact angle on a planar surface at 25° C., has a water contact angle of less than 70°, preferably at least less than 60° and particularly preferably less than 50°.

Biocompatibility layer B according to the invention is preferably resistant to manual wiping with isopropanol-impregnated two-ply cosmetic and all-purpose wipes consisting of soft tissue (produced for example by TEMCA GmbH). Also preferably, the layers to be used according to the invention have a modulus of elasticity of more than 3.0 CPa or a hardness of more than 0.4 GPa, more preferably a modulus of elasticity of more than 5.0 GPa or a hardness of more than 0.5 GPa, measured in each case by means of nano-identification, the measuring method described above being used.

Also preferred is a biocompatibility layer B which has a proportion of 5-20% of carbon atoms with a bond to precisely two oxygen atoms ("COO"), measured by XPS. Accordingly, 5-20% of the carbon atoms of the silicon-containing layer are present as ester or acid groups. More preferred is a proportion of 5-10%. These polar groups also require the hydrophilicity of the biocompatibility layer according to the invention. In particular, these configurations also prefer the adhesion of biomolecules, such as most particularly albumin and fibromectin, which in turn improves the cell growth.

The proportion of carbon atoms with a bond to precisely one oxygen atom ("C—O") and to precisely two oxygen atoms ("COO") is determined in that the XPS spectra which have been measured oriented to the sample standard are subjected to a curve fitting. Assuming that the nitrogen concentration in the coating is low (<0.5 atom %), the chemical shifts are interpreted at the C1s spectrum, as stated in Table 1:

TABLE 1

| Abbreviation | Peak number (in FIG. 3-8) | Groups | Bond energy |
| --- | --- | --- | --- |
| "C" | I | Aliphatic | 285.0 eV |
| "C—O" | II | Alcohol, Ether | 286.5 ± 0.2 eV |
| "COO" | III | Carboxyl, Ester | 289.2 ± 0.2 eV |

The aliphatic carbon is set at 285.0 eV per definition. To prepare the curve fitting, a baseline correction of the C1s spectrum is made according to Shirley in the range of from 281 eV to 292 eV. Fitting is then performed using Gauβ-Lorentz functions. For this purpose, the maximum of the bond energy for the aliphatic carbon is placed at 285.0 eV, the maximum of the "C—O" carbon is placed at 286.5 eV and at 289.2 eV for the "COO" carbon. The energy in the region of ±0.2 eV, the counting rate and the half width are set as fit parameters. In this respect, the half width is established at a maximum of 1.4 eV. The bond energy of the aliphatic carbon is not also fitted. The fit is ended when the least square fit algorithm assumes its minimum. The group-specific concentrations can be calculated from the surface ratios of the function for the aliphatic carbon or for the functions for "C—O" and "COO" carbon. Furthermore, in the quantification of the concentrations, it is assumed that the functional groups are distributed homogeneously in the entire information depth of the XPS spectrum, so that the measured coating must be at least 10 nm thick.

The non-genotoxic layer is produced or can be produced by plasma polymerization of a methylsiloxane precursor, preferably hexamethyldisiloxane, in particular by low pressure or atmospheric pressure plasma polymerization, or by crosslinking a silicone oil without chemically reactive groups under the effect of a plasma or UV radiation of a wavelength of less than 250 nm, in particular excimer radiation.

In the present context, a "plasma polymeric" layer is a layer which can be produced by plasma polymerization. Plasma polymerization is a process in which gaseous precursors (often also called monomers), excited by a plasma are precipitated on a freely selectable substrate as a highly crosslinked layer. The prerequisite for a plasma polymerization process is the presence of chain-forming atoms, such as carbon or silicon in the working gas. The excitation fragments the molecules of the gaseous substance (precursors) by the bombardment by electrons and/or high energy ions. In so doing, highly excited radical or ionic molecule fragments are produced which react together in the gas chamber and are deposited on the surface to be coated. The electrical discharge of the plasma and the intensive ion and electron bombardment acts constantly on this deposited layer, so that further reactions can be initiated and a high-grade linking (crosslinking) of the deposited molecules can be achieved in the deposited layer.

Combinations of the coating processes are also possible, for example the plasma crosslinking of silicone oil combined with a plasma coating.

In the latter case, a substance which contains chain-forming atoms such as carbon or silicon, for example silicone oil is applied first of all to the surface (for example of the substrate) as the liquid film. If the liquid film is exposed to a plasma, the electrons and/or high energy ions and the UV radiation generated in the plasma act on the liquid molecules. Bond breakages occur in the liquid, resulting in a crosslinking of the liquid molecules. A person skilled in the art can achieve a suitable crosslinking degree of the liquid film via the amount of exposure.

In the present context, the term "plasma polymeric layer" also includes layers which can be produced by plasma-assisted CVD (PE-CVD).

It is furthermore explicitly mentioned that atmospheric pressure plasma processes can also be used to produce plasma polymeric layers to be used according to the invention, although low pressure plasma polymerization processes are presently preferred.

In the present context, substances which are supplied as gas or vapor to a plasma for layer formation by plasma polymerization are called "monomers" (gaseous precursors). Liquids which can be crosslinked, for example by the effect of a plasma (for example by highly excited particles, electrons or UV radiation), without previously evaporating are called "liquid precursors".

Plasma polymeric layers are to be clearly distinguished in their chemical and structural composition from polymeric layers. Whereas for polymers the linking process of the monomers takes place in a predictable manner, in plasma polymerization the monomers used are fragmented (to complete destruction) and are deposited in the form of reactive species so that a crosslinked layer is produced, without areas with regular repeat units. This resulting layer is additionally exposed to the plasma so that it is further modified by ablation and redeposition effects. The resulting layer is crosslinked three-dimensionally and is amorphous. Thus, in the present context, plasma polymerization differs from conventional methods of polymerization. This also applies to so-called "structure-preserving plasma polymerization", because even in the case of "mild" plasma conditions, unpredictable molecule breaks occur. In this connection, reference is made, for example to the following citation: "Plasma Polymerization" by H. Yasuda, Academic Press, Inc., (1985).

After a non-genotoxic layer to be used according to the invention has been produced by crosslinking the precursor or silicone oil, said layer can be at least partially oxidized, preferably by plasma effect ("activation"), flame treatment, oxyfluorination, laser treatment or a treatment with excimer lamps. The chemical composition of the surface of the coating can be simply adjusted in a defined manner in particular by oxidation. In this way, it is possible for example to provide the different articles according to the invention listed above with a biocompatibility layer B, in particular with a layer on which, immediately after production, a water contact angle of not more than 35° is established in order to enjoy the advantages listed above. In particular in this way, the specific substance ratios described above (in particular C—O/COO bond proportions) can be adjusted in a surprisingly effective manner, which promotes an adhesion of biomolecules.

By adjusting the chemical surface composition in general, it is possible in particular to promote an adhesion of tissue cells, preferably with a biocompatibility layer B, and/or to reduce an adhesion of tissue cells, preferably with a biocompatibility layer A, and/or to reduce an adhesion of tissue cells on part of the surface of the biocompatible article, preferably with a biocompatibility layer A and to promote the adhesion on another part of the surface of the non-genotoxic article, preferably with a biocompatibility layer B, and/or to reduce an adhesion of pathogenic settlements, preferably with a biocompatibility layer A, and/or to reduce an adhesion of bacteria and/or to reduce thrombogenesis and/or to reduce the occurrence of humoral and cellular immune reactions and/or to reduce unspecific adsorption of peptides, proteins, lipids and/or nucleic acids on the surface of the non-genotoxic article, preferably with a biocompatibility layer A, and/or to allow spatially restricted growth of cell cultures on the surface of the biocompatible article, preferably by providing only part of the surface with a non-genotoxic layer to be used according to the invention, preferably with a biocompatibility layer B, and/or to increase the wettability by aqueous fluids, in particular blood, preferably with a biocompatibility layer B.

To delimit the area to be oxidized of the non-genotoxic layer, preferably a mask which is positioned in a material-bonding manner, preferably a detachable self-adhesive mask, more preferably an adhesive tape, and/or a substance which is at least partially soluble, preferably in water, or a printed mask is used and is preferably removed after oxidation. In this way, it is possible to delimit the oxidized area in a particularly simple manner.

By simple masking or, for example local laser treatment, it is possible to realize both growth-promoting and growth-inhibiting surface regions on one and the same component. For example, to inhibit growth, biocompatibility layer A is applied and to promote growth, biocompatibility layer B is applied or biocompatibility layer A is transformed by oxidation into biocompatibility layer B.

The advantage of a partial coating or of different coatings (in turn preferably produced by providing appropriate maskings) is in particular that here locally different characteristics (improved/reduced adhesion) can be realized very easily in the corresponding places of the article according to the invention. In this respect, the initially complete coating of the article with a non-genotoxic layer according to the invention, for example biocompatibility layer A, is particularly economical if subsequently selected areas are transformed by oxidation into a non-genotoxic layer according to the invention, for example into biocompatibility layer B. In this way, different surface characteristics are achieved while maintaining non-genotoxicity and while only once using appropriate masks or coating delimitations.

The non-genotoxic layer preferably has a layer thickness of not more than 2 µm, preferably not more than 1 µm, more preferably not more than 500 nm, and respectively of at least 5 nm, preferably at least 10 nm and more preferably at least 15 nm.

According to the invention, in particular a non-genotoxically coated article is also specified, comprising a non-genotoxic layer as described above. The layer is preferably arranged on an outer and/or inner surface of the described article according to the invention. The layer is expediently arranged on the surface which, in the intended use of the article, comes into contact with the material to be protected, thus for example the inside of a syringe or the outside of a bone attaching nail.

Part of the invention is also the use of a non-genotoxic layer for influencing, modifying or altering the cytotoxicity, measured according to ISO 10993-5:2003, irritations or intracutaneous reactivity, measured according to ISO 10993-10:2003, systemic toxicity (acute toxicity, subacute toxicity and subchronic toxicity), measured according to ISO 10993-11:2003, implantation compatibility, measured according to ISO 10993-6:2003, and/or hemocompatibility, measured according to ISO 10993-4:2003 of an article.

The object of the invention was to specify means with which the transfer of functional layers to optionally occurring substrate surfaces can be performed cleanly, with a good coating quality and in a manner which can be effectively integrated into working processes which are already known.

Biocompatibility layer A is preferably used for the following applications:

angioplasty balloons cannulas blood preserving pouches sensors containers for receiving and/or transporting bodily fluid, tissue or the constituents thereof of a living being or of biomolecules or active substances produced therewith catheters, such as bladder catheters, coronary catheters or insulin catheters on the surfaces which are not to grow in blood vessel stents in the internal region artificial organs such as artificial kidneys or hearts, on the surfaces on which in-growth is undesired pacemakers and a power source thereof, on the surfaces on which in-growth is undesired, for example surfaces which have to be exposed to renew the power supply artificial heart valves, on the surfaces on which in-growth is undesired, as on the valve surface cell culture containers artificial corneas, on surfaces on which the settling of cells must be prevented, as in the central region responsible for through-vision fermenters, in which interactions with the reactor surface are undesired pumps or other devices for releasing substances in the body, on the surfaces which are not to be covered by cells.

Biocompatibility layer B is preferably used for the following applications:

implants (endoprostheses) such as bone attaching nails, medical nails, clasps, threads, screws cochlea implants heart valve rings intraocular lenses fermenters in which an interaction with the wall surface is desired, for example in the sense of a heterogenic or heterogenized catalysis, more preferably when cells or biologically producible macromolecules are fixed to the reactor surfaces for the reactions probes, such as percutaneous endoscopic jejunostomy probes filter material for filtering cells and/or biologically producible macromolecules out of a fluid biocompatible scaffolds articles for at least partially covering skin or mucous membrane or wounds of a living being, such as wound dressings, plasters, contact lenses, incontinence products, pumps or other devices for releasing substances in the body, on the surfaces which are supposed to grow in prostheses (open implants, epitheses) in the region of passage through the skin or tissue ports in the region of the passage through the skin or tissue artificial joint mouse, such as sockets and a counterpart cooperating therewith, for example for hip joints wound dressings catheters such as bladder catheters, coronary catheters, insulin catheters in areas in which in-growth is desired, particularly for long-term catheters blood vessel stents on the surfaces directed towards to the vessel wall injection systems on surfaces on which in-growth is desired, particularly in regions of passage through the skin or tissue artificial organs such as artificial kidneys or hearts, particularly on plastics material surfaces for which in-growth is desired pacemakers and a power source thereof, on areas for which in-growth is desired, such as electrodes, wires and housing—the latter particularly on the surfaces which are not moved when the power source is replaced cell culture containers, for which growth of cells on the container is desired artificial cornea in the peripheral region which is to grow in.

In the following, the invention will be described in more detail with reference to the examples and figures, without thereby restricting the scope of protection of the claims.

In the accompanying FIGS. 1 to 16:

FIG. 1: shows the XPS general spectrum of coating plasma polymer A1

Figure 2:
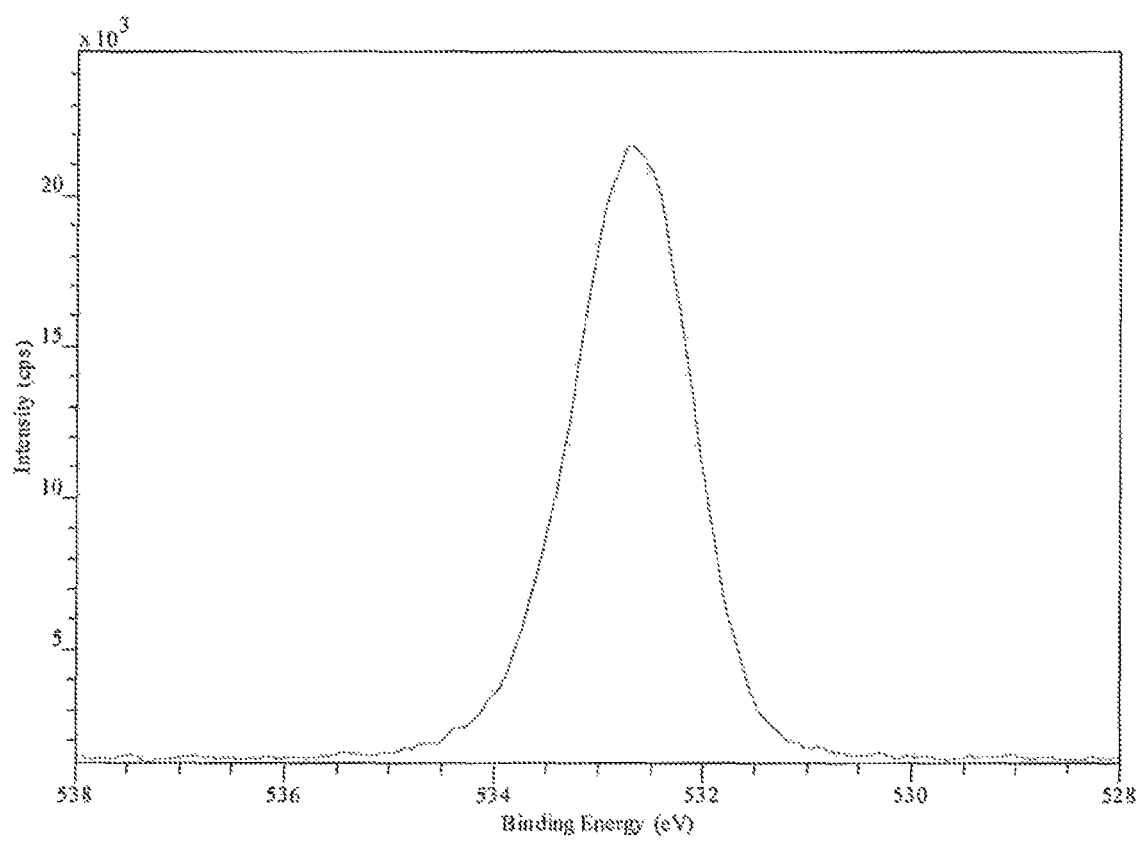

FIG. 2: shows the XPS detail spectrum of the O 1s peak of coating plasma polymer A1

Figure 3:
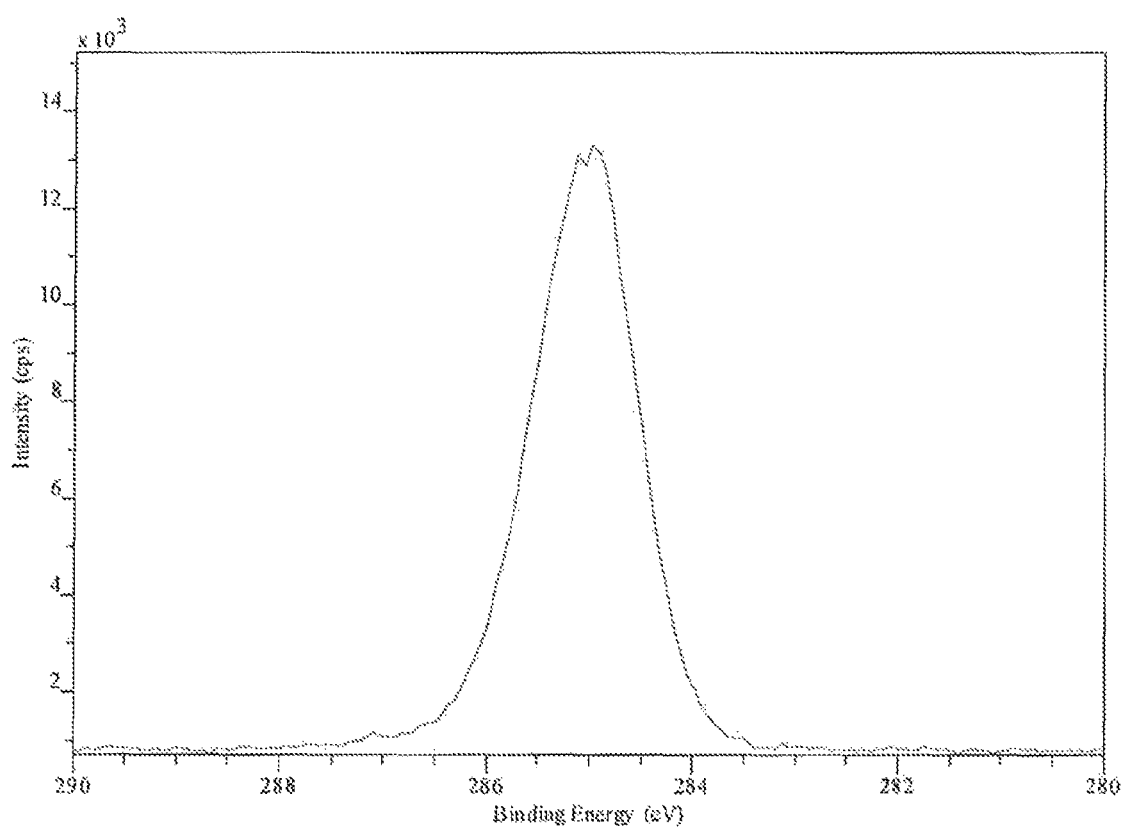

FIG. 3: shows the XPS detail spectrum of the C 1s peak of coating plasma polymer A1

Figure 4:
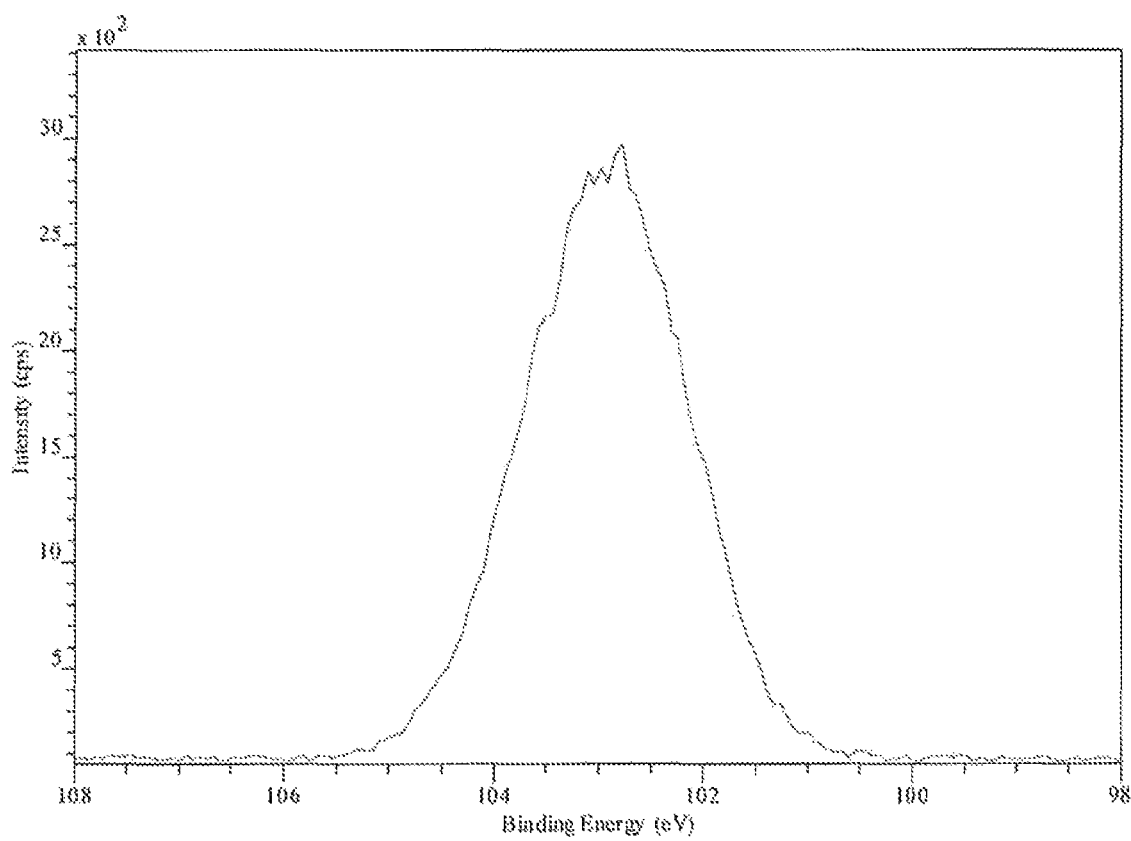

FIG. 4 shows the XPS detail spectrum of the Si 2p peak of coating plasma polymer A1

Figure 5:
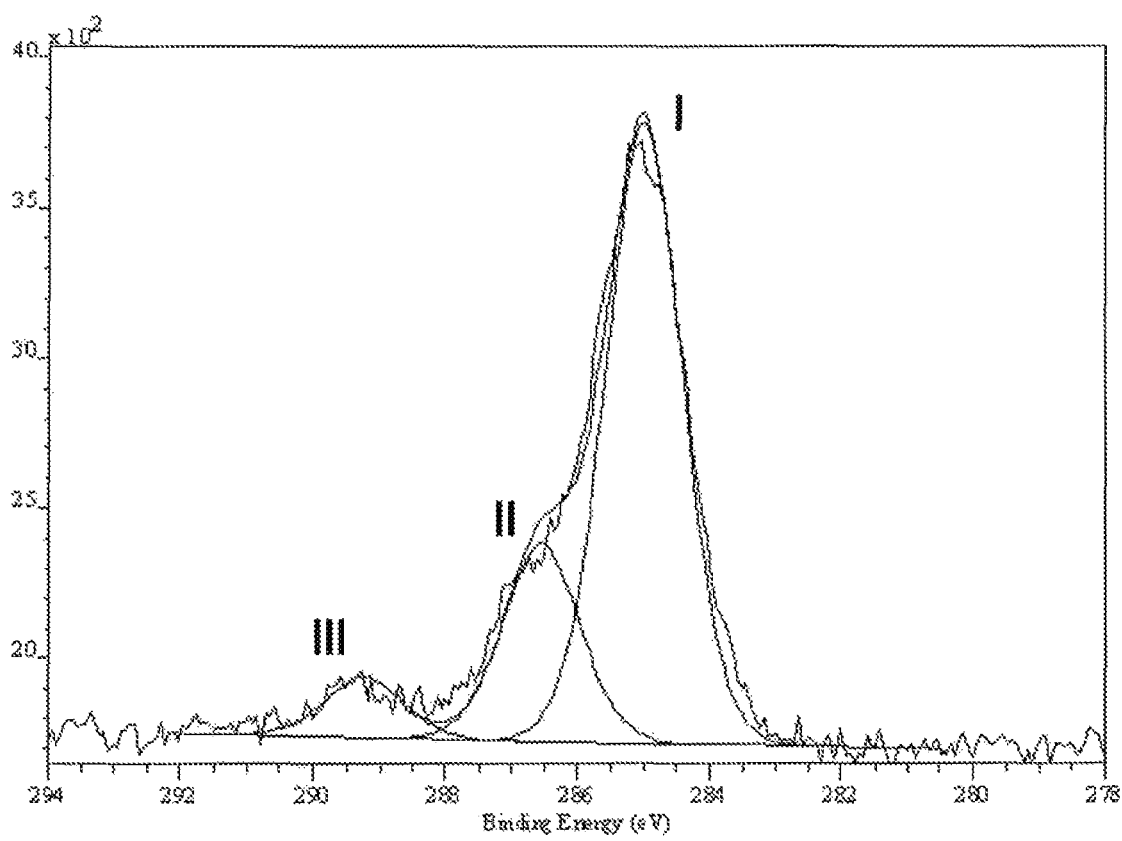

FIG. 5: shows the C1s spectrum of coating plasma polymer B4

Figure 6:
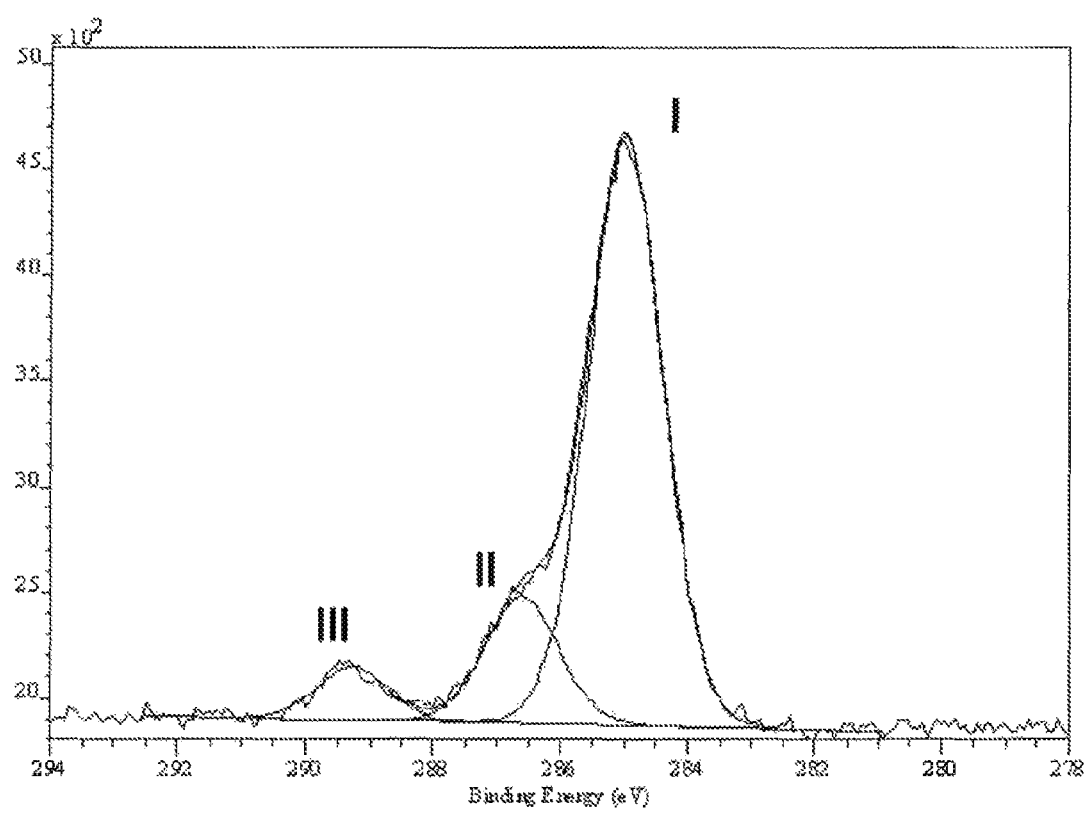

FIG. 6: shows the C1s spectrum of coating plasma polymer B5

Figure 7:
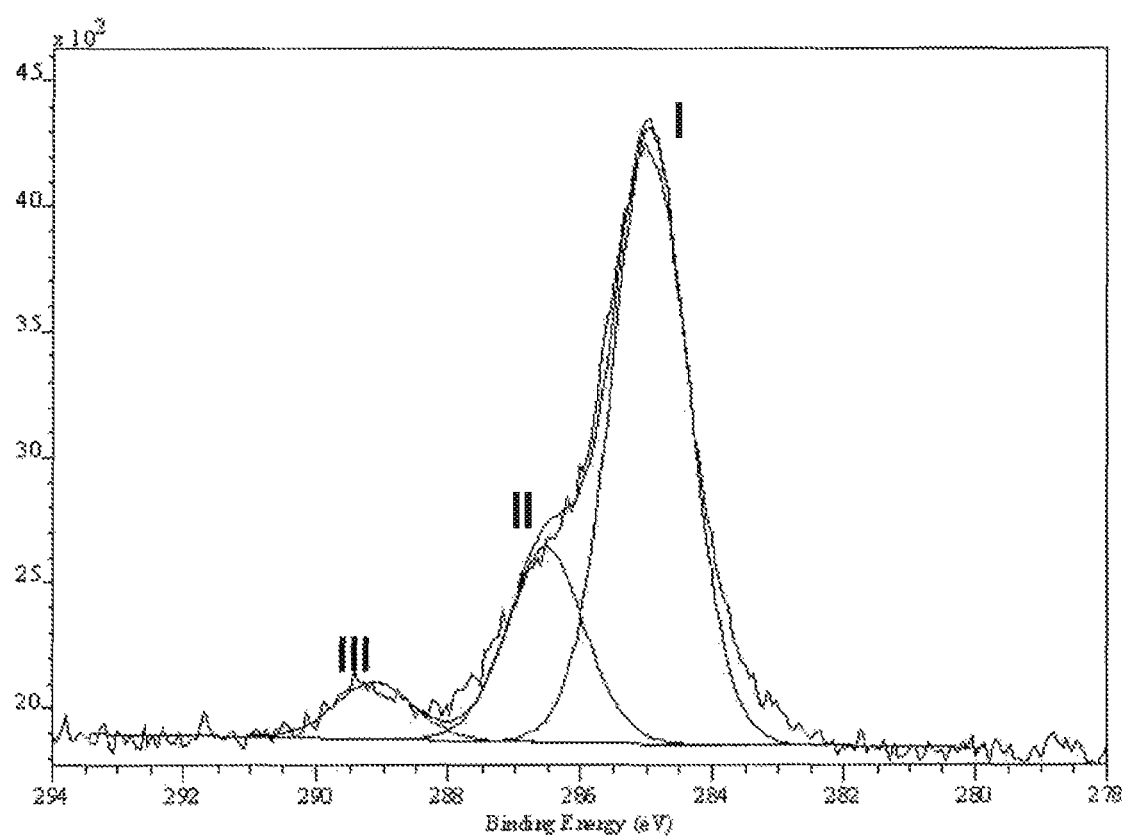

FIG. 7: shows the C1s spectrum of coating plasma polymer B6

Figure 8:
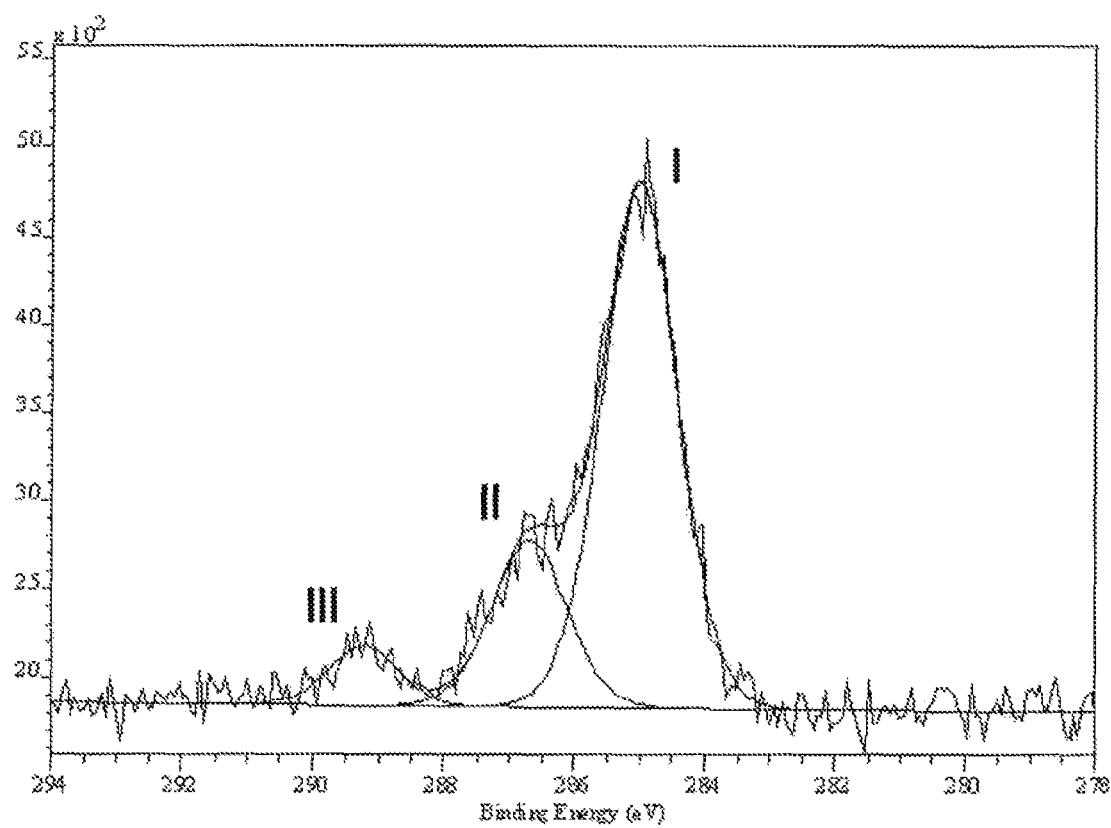

FIG. 8: shows the C1s spectrum of coating plasma polymer B7

Figure 9:
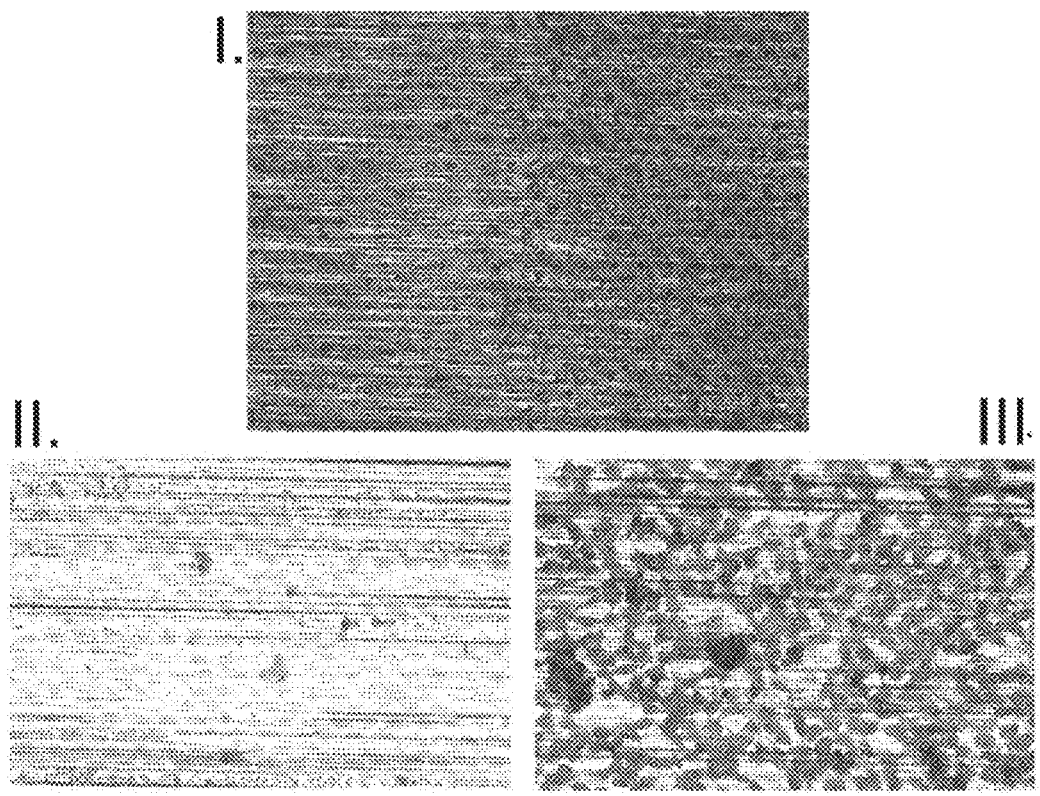
Figure 10:
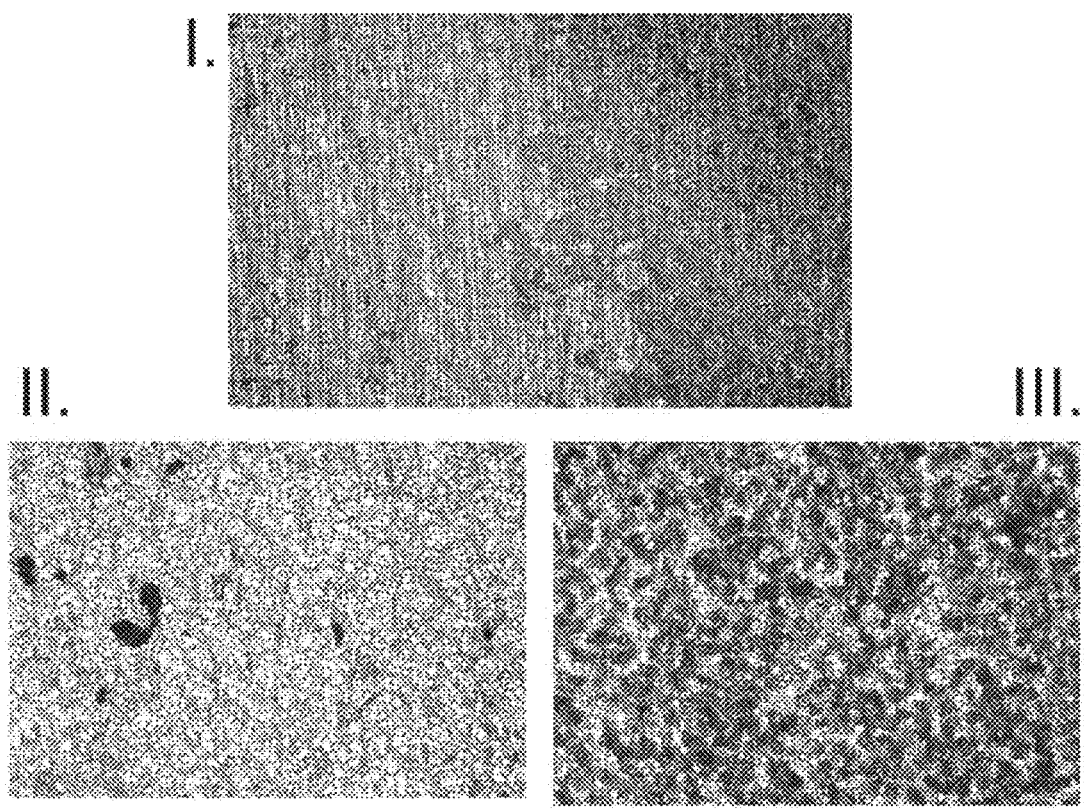
Figure 11:
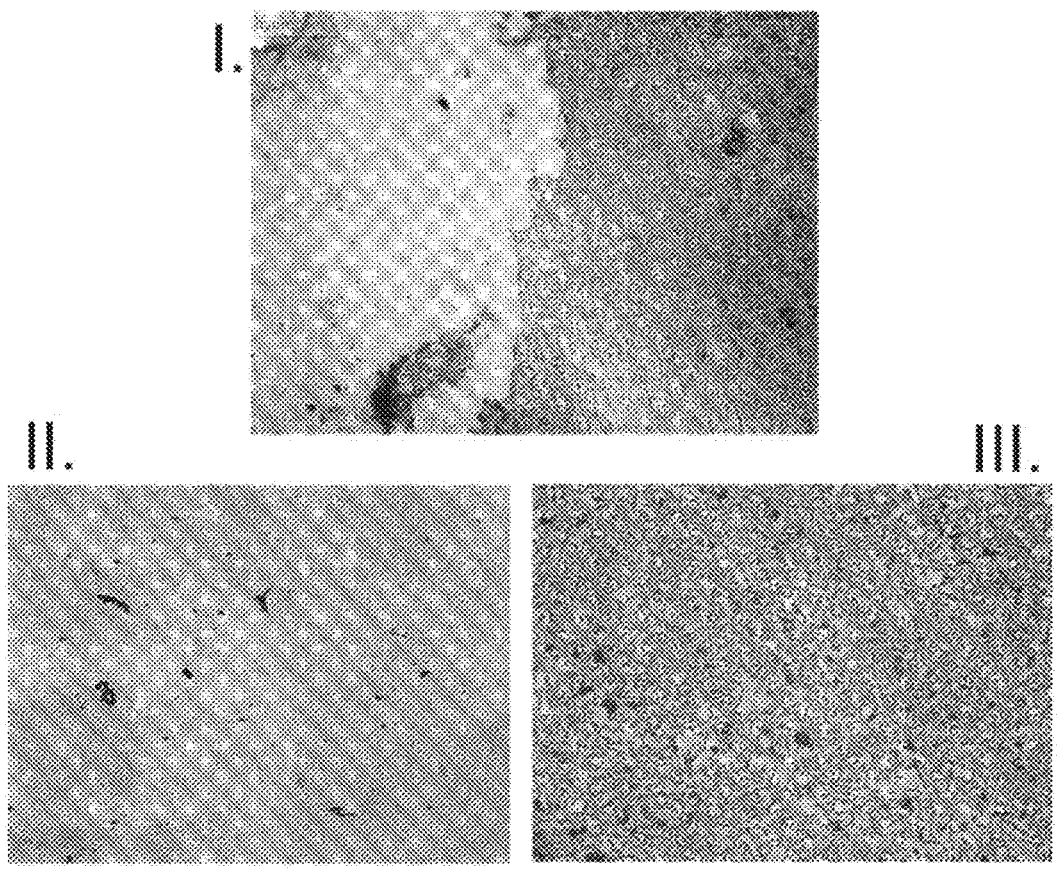
Figure 12:
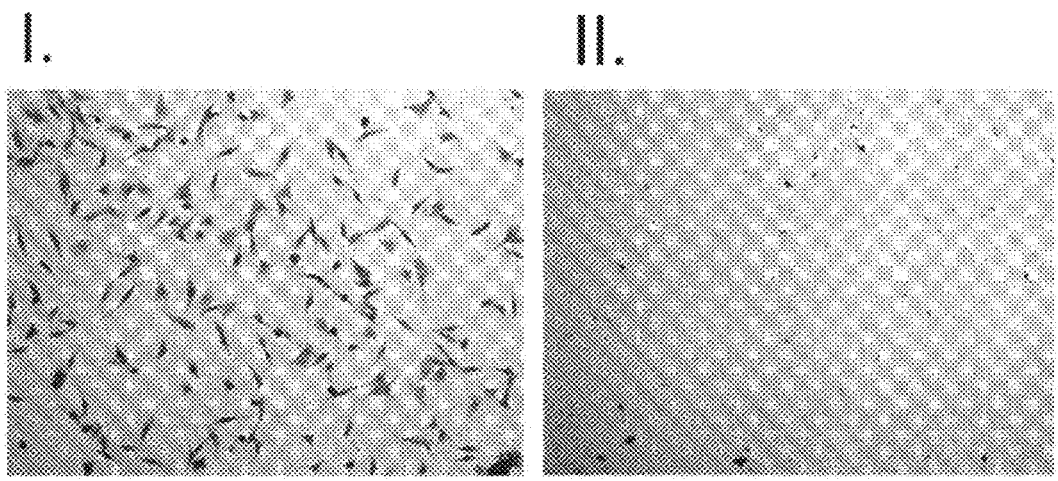
Figure 13:
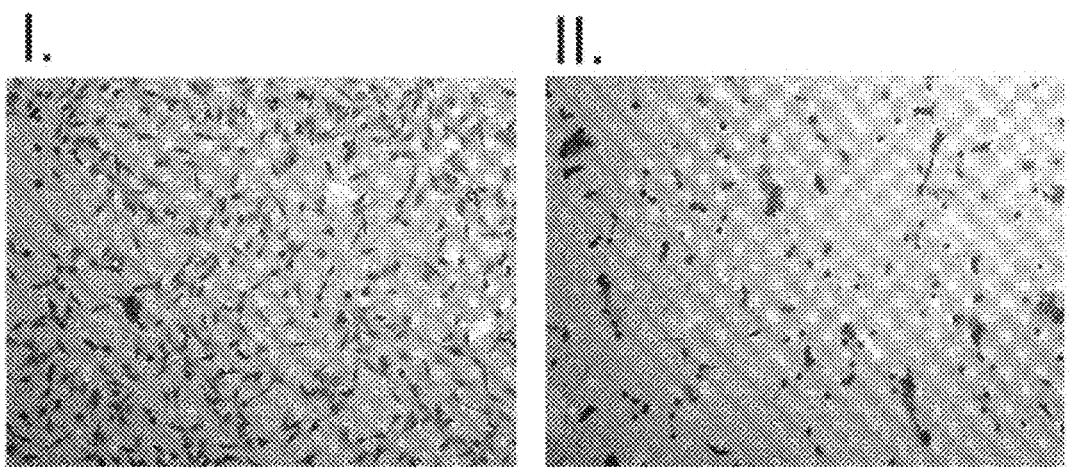
Figure 14:
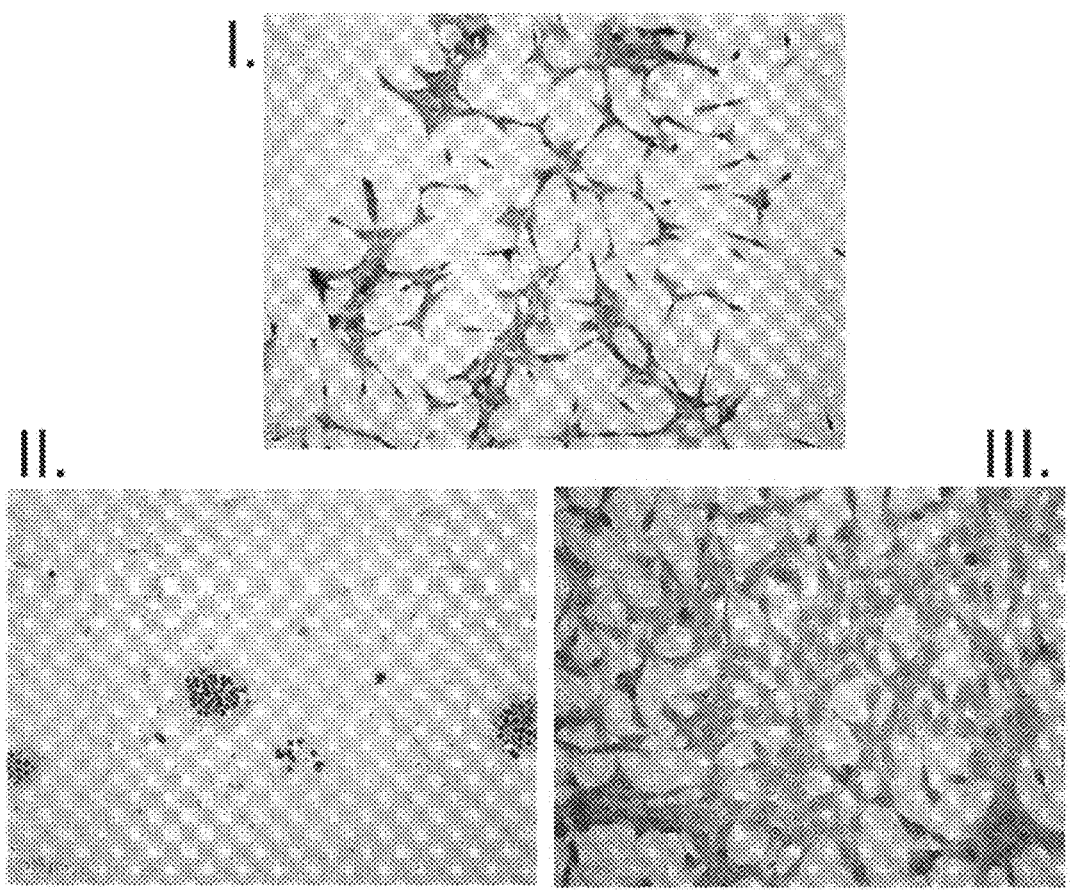
Figure 15:
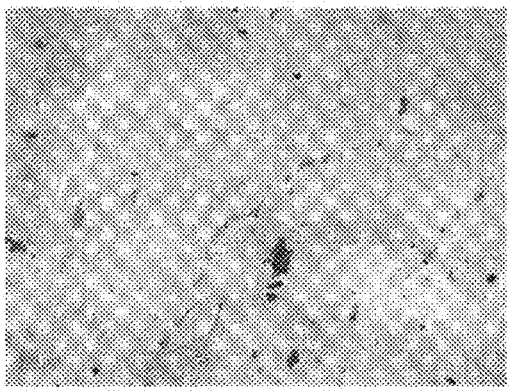
Figure 15:
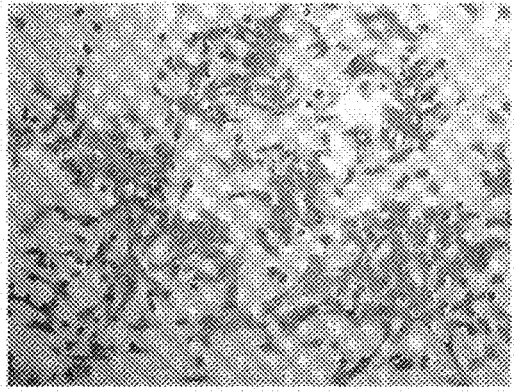
Figure 16:
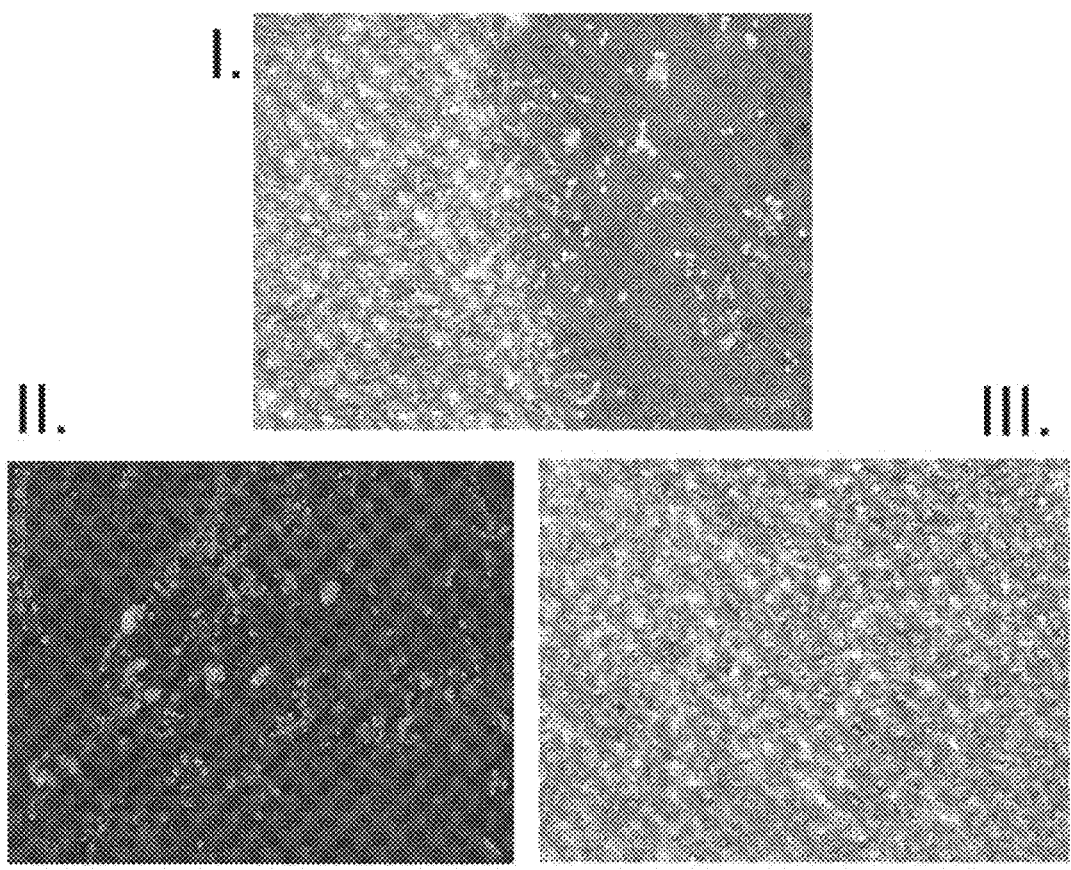
Figure 17:
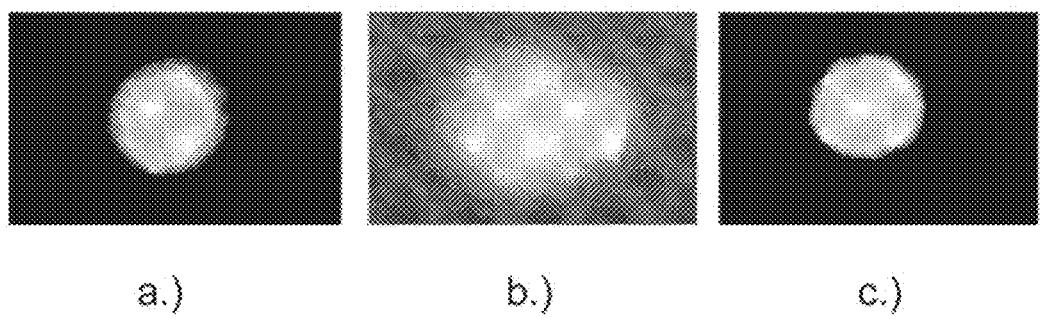

FIG. 9: shows the cell growth management by biocompatibility layers on aluminum FIG. 10: shows the cell growth management by biocompatibility layers on stainless steel FIG. 11: shows the cell growth management by biocompatibility layers on glass FIG. 12: shows the cell growth management by biocompatibility layers using excimer lamps on glass FIG. 13: shows the cell growth management by biocompatibility layers on ceramics FIG. 14: shows the cell growth management by biocompatibility layers on PMMA FIG. 15: shows the cell growth management by biocompatibility layers on silicone FIG. 16: shows the cell growth management by biocompatibility layers on titanium FIG. 17: shows the test for genotoxicity according to DIN ISO 10993-3 using the comet assay. Images show on the left: negative control without DNA fragmenting, centre: positive control with pronounced tail and right: biocompatibility layer U1 without DNA fragmenting.

EXAMPLES

Example 1

Plasma Polymeric Coatings from a 1 $m^3$ Reactor

Flat substrates of the materials stated below were provided with a layer according to the invention by a low pressure plasma process in a 1 $m^3$ reactor (for description see ISBN 978-3-86727-548-4 "Scaling of plasma polymeric coating processes", pages 21-26 by Dr. Klaus Vissing):

aluminum as sections (approx. 10×10 mm)

stainless steel as sections (approx. 10×10 mm)

glass as sections (approx. 10×10 mm)

aluminum oxide ceramics A123 (from Degussit-Friatec)

polymethylmethacrylate (PMMA) as sections (approx. 10×10 mm) from sterile packaging bottles silicone as sections (approx. 15*10 mm)

titanium as sections (approx. 15*10 mm)

The samples were finely cleaned with oxygen in the plasma according to the prior art and activated according to requirements and/or provided with an adhesion-promoting layer. The plasma polymeric coating according to the invention was then applied at a frequency of 13.56 MHz, $O_2$ and hexamethyldisiloxane (HMDSO) being supplied to the plasma. The precise process parameters for the deposition of the plasma polymeric coating are stated in Table 2. The period of time for the plasma polymeric coating varied from 9 to 60 minutes. Layers varying in thickness between 90 and 250 nm were applied. The pump-out time for plasma polymer A6 was 8.5 minutes.

TABLE 2

| Coating | Gas flow HMDSO (Sccm) | Gas flow $O_2$ (Sccm) | Gas flow $H_2$ (Sccm) | Pressure (mbar) | Power (W) |
| --- | --- | --- | --- | --- | --- |
| Plasma polymer A1 | 67 | 20 | | 0.025 | 700 |
| Plasma polymer A2 | 27 | 20 | 200 | 0.025 | 1600 |
| Plasma polymer A3 | 27 | 100 | | 0.023 | 2500 |
| Plasma polymer A4 | 60 | 200 | | 0.020 | 700 |
| Plasma polymer A5 | 30 | 200 | | 0.020 | 700 |
| Plasma polymer A6 | 30 | 200 | | 0.024 | 1600 |

FIGS. 1 to 4 show XPS spectra of the coating plasma polymer A1.

Furthermore, plasma polymeric coatings were produced under conditions as described in Table 3, analogously to the process described for plasma polymers A1 to A3 and were activated for 60 seconds in the low pressure plasma in a further process step. The process parameters for the plasma polymeric coating and the activation are stated in Table 3 for these layers which allowed an improved adhesion of biomolecules and cells. The time period for the plasma polymeric coating varied between 12 and 19 minutes. Layers of between 50 and 170 nm were applied.

TABLE 3

| | Coating process step | | | | Activation process step | | |
| --- | --- | --- | --- | --- | --- | --- | --- |
| | Gas flow | | | | Gas flow | | |
| Coating | HMDSO (Sccm) | $O_2$ (Sccm) | Pressure (mbar) | Power (W) | $O_2$ (Sccm) | Pressure (mbar) | Power (W) |
| Plasma polymer B1 | 13 | 500 | 0.025 | 2000 | 500 | 0.025 | 2000 |

TABLE 3-continued

| | Coating process step | | | | Activation process step | | |
|---|---|---|---|---|---|---|---|
| | Gas flow | | | | Gas flow | | |
| Coating | HMDSO (Sccm) | O$_2$ (Sccm) | Pressure (mbar) | Power (W) | O$_2$ (Sccm) | Pressure (mbar) | Power (W) |
| Plasma polymer B2 | 10 | 500 | 0.03 | 2000 | 500 | 0.03 | 2000 |
| Plasma polymer B3 | 10 | 500 | 0.03 | 2000 | 500 | 0.025 | 2000 |

In addition, plasma polymeric coatings were also produced under conditions described in Table 4 analogously to the process described for plasma polymers A1 to A3 and were activated for a short time in the low pressure plasma in a further step. The process parameters for the plasma polymeric coating and the activation are stated in Table 3 for the resulting layers which allowed a moderate to good adhesion of biomolecules and cells. The coating time for the plasma polymeric coating was 35 minutes. Layers which were 104 nm and 110 nm thick were applied.

TABLE 4

| | Coating process step | | | | Activation process step | | | |
|---|---|---|---|---|---|---|---|---|
| | Gas flow | | | | Gas flow | | | |
| Coating | HMDSO (Sccm) | O$_2$ (Sccm) | Pressure (mbar) | Power (W) | O$_2$ (Sccm) | Pressure (mbar) | Power (W) | Time (s) |
| Plasma polymer U1 | 67 | 20 | 0.027 | 700 | 500 | 0.032 | 2000 | 10 |
| Plasma polymer U2 | 67 | 20 | 0.027 | 700 | 500 | 0.032 | 2000 | 30 |

Explanation of the XPS Measurements

The XPS tests were carried out using the spectrometer KRATOS AXIS Ultra manufactured by Kratos Analytical. The analysis chamber was equipped with an X-ray source for monochromatized Al K$_\alpha$ radiation, an electron source as neutralizer and a quadrupol mass spectrometer. The installation also had a magnetic lens which focused the photoelectrons via an inlet slot into a hemispherical analyzer. The aliphatic proportion of the C 1s peak was set at 285.0 eV by calibration. During the measurement, the surface normal was directed at the inlet slot of the hemispherical analyzer.

When determining the substance ratios, the fit energy was in each case 160 eV, the corresponding spectra are called general spectra. When determining the detail spectra, the fit energy was in each case 20 eV.

The mentioned measuring conditions are preferred to allow the type of spectrometer to be substantially independent and to identify plasma polymeric products according to the invention.

The polydimethylsiloxane, silicone oil DMS-T23E produced by Gelest Inc. (Morrisville, USA) was used as reference material. This trimethylsiloxy-terminated silicone oil has a kinematic viscosity of 350 mm$^2$/s (±10%) and a density of 0.970 g/ml at 25° C. and an average molecular weight of approximately 13,650 g/mol. The selected material is characterized by an extremely low proportion of constituents which can be evaporated: after 24 hours at 125° C. and 10$^{-5}$ Torr, less than 0.01% of volatile fractions were detected (according to ASTM-E595-85 and NASA SP-R0022A). It was applied to a silicon wafer as a 40 or 50 nm thick layer by a spin coating process; hexamethyldisiloxane was used as solvent.

The results of the XPS measurements which have been described are stated in Table 5. The atomic composition is based on 100% for the total of the elements silicon, oxygen and carbon. The content of further elements was either below the detection limit or, as in the case of nitrogen, below 0.2%. For the curve fitting, three signals were assumed with the bond energies stated in Table 1. Comparative simulations with an additional signal at approximately 288.0 eV produced no significant proportion (i.e. a proportion of >1% of C signals) of this bond energy which would be characteristic of, for example aldehyde and keto groups ("C═O"). This is also generally preferred for the layers to be used according to the invention.

TABLE 5

| Plasma polymer | Atomic composition (at %) | | | Ratios | | | Curve Fitting (% of C-total) | | |
|---|---|---|---|---|---|---|---|---|---|
| | O 1s | C 1s | Si 2p | C/Si | O/Si | O/C | C | C—O | COO |
| A1 | 25.1 | 50.8 | 24.1 | 2.1 | 1.0 | 2.0 | 96.6 | 3.4 | 0.0 |
| A6 | 49.7 | 23.0 | 27.4 | 0.8 | 1.8 | 0.5 | 93.3 | 6.7 | 0.0 |
| U1 | 46.1 | 29.4 | 24.6 | 1.2 | 1.9 | 0.6 | 88.7 | 8.8 | 2.5 |
| U2 | 58.7 | 15.1 | 25.2 | 0.6 | 2.3 | 0.3 | 73.4 | 18.5 | 8.2 |
| B1 | 59.1 | 13.2 | 27.8 | 0.5 | 2.1 | 0.2 | 76.2 | 14.6 | 9.2 |

Example 2

Plasma Polymeric Compositions from a 250 l Reactor

The plasma polymeric coatings B4 to B9 (see below) were produced using a low pressure plasma reactor having a volume of 250 l (description in ISBN 3-8265-9216-6 "Characterization of the spectroscopic characteristics of metal and semiconductor clusters in plasma polymeric matrices" by Dr. Dirk Salz). The electrical excitation voltage has a frequency of 13.56 MHz. The distance between the plasma discharge electrode and the substrate (silicon wafer) was 30 cm. Before each experiment, the low pressure reactor was evacuated to a pressure of 0.01 mbar. The residual gas at this pressure consists to more than 95% of water vapor. The coatings were tested by XPS. The C1s spectra were subjected to a curve fitting. Furthermore, the contact angle of water with continuous drops was measured at 25° C. on the coated silicon wafers within a period of less than 12 hours.

Practical Example Plasma Polymer B4

Two silicon wafers were coated in three process steps. In the first step, an oxygen cleaning procedure was carried out, followed by the coating step with hexamethyldisiloxane and finally oxygen activation. The precise coating parameters are given in Table 6. Layers with a thickness of approximately 60 nm were produced. The water contact angle was 23°.

TABLE 6

Coating parameters of Practical Example plasma polymer B4

|  | Fine cleaning | Coating | Activation |
| --- | --- | --- | --- |
| $O_2$-Flow/sccm | 60 | 60 | 60 |
| HMDSO-flow/sccm | 0 | 5 | 0 |
| Plasma power/W | 800 | 800 | 800 |
| Treatment time/min | 10 | 10 | 10 |
| Process pressure/mbar | 0.022 | 0.026 | 0.022 |

The XPS analysis provides the atomic composition of oxygen=65.9%, silicon=27.0%, carbon=7.03%, nitrogen=0.12%. FIG. 5 shows the experimentally determined high resolution C1s spectrum as an envelope of the three individual Gauβ-Lorentz functions which have been determined by a curve fit. The surface quantification produces the following result for carbon: aliphatic carbon proportion=77.1% (285 eV), C—O groups=16.5% (286.6 eV) and COO groups=6.4% (289.3 eV). The numbers in brackets correspond to the energetic maximum of the Gauβ-Lorentz functions. Comparative simulations with an additional signal at 288.0 eV produced a proportion of this bond energy of less than 1% (for this and the following corresponding simulations naturally based on the entirety of the C 1s signals).

Practical Example Plasma Polymer B5

This experiment was carried out as for Practical Example B4, but the activation time was 20 min instead of 10 min.

TABLE 7

Coating parameters of Practical Example plasma polymer B5

|  | Fine cleaning | Coating | Activation |
| --- | --- | --- | --- |
| $O_2$-Flow/sccm | 60 | 60 | 60 |
| HMDSO-Flow/sccm | 0 | 5 | 0 |
| Plasma power/W | 800 | 800 | 800 |
| Treatment time/min | 10 | 10 | 20 |
| Process pressure/mbar | 0.022 | 0.026 | 0.022 |

The layer thickness and the water contact angle on the Si wafers were respectively 60 nm and 13°. The XPS analysis provides the following atomic composition: oxygen=66.2%, silicon=27.4%, carbon=6.29%, nitrogen=0.13%. The result of the curve fit (FIG. 6) produces the following concentrations for carbon: aliphatic carbon proportion=76.8% (285 eV), C—O groups=16.4% (286.5 eV) and COO groups=6.8% (289.2 eV). Comparative simulations with an additional signal at 288.0 eV produced a proportion of this bond energy of less than 1%.

Practical Example Plasma Polymer B6

This experiment was carried out as for Practical Example B4, but activation took place with water vapor which is constantly desorbed from the reactor walls.

TABLE 8

Coating parameters of Practical Example plasma polymer B6

|  | Fine cleaning | Coating | Water vapor plasma |
| --- | --- | --- | --- |
| $O_2$-Flow/sccm | 60 | 60 | 0 |
| HMDSO-Flow/sccm | 0 | 5 | 0 |
| Plasma power/W | 800 | 800 | 800 |
| Treatment time/min | 10 | 10 | 10 |
| Process pressure/mbar | 0.022 | 0.026 | 0.022 |

The layer thickness and the water contact angle on the Si wafers were respectively 60 nm and 5°. The XPS analysis provides for the first 10 nm the following atomic composition: oxygen=65.7%, silicon=27.2%, carbon=6.96%, nitrogen=0.12%. The result of the curve fit (FIG. 7) produces the following concentrations for carbon: aliphatic carbon proportion=73.4% (285 eV), C—O groups=21.2% (286.5 eV) and COO groups=5.4% (289.1 eV). Comparative simulations with an additional signal at 288.0 eV produced a proportion of this bond energy of less than 1%.

Practical Example B7

This experiment was carried out as for Practical Example B5, but activation took place for 20 min with water vapor which is constantly desorbed from the reactor walls.

TABLE 9

Coating parameters of Practical Example plasma polymer B7

|  | Fine cleaning | Coating | Water vapor plasma |
| --- | --- | --- | --- |
| $O_2$-Flow/sccm | 60 | 60 | 0 |
| HMDSO-Flow/sccm | 0 | 5 | 0 |
| Plasma power/W | 800 | 800 | 800 |
| Treatment time/min | 10 | 10 | 20 |
| Process pressure/mbar | 0.022 | 0.026 | 0.022 |

The layer thickness and the water contact angle on the Si wafers were respectively 60 nm and approximately 0°. The XPS analysis provides for the first 10 nm the following atomic composition: oxygen=65.5%, silicon=26.9%, carbon=7.44%, nitrogen=0.14%. The result of the curve fit (FIG. 8) produces the following concentrations for carbon: aliphatic carbon proportion=70.4% (285 eV), C—O groups=22.4% (286.7 eV) and COO groups=7.1% (289.2 eV). Comparative simulations with an additional signal at 288.0 eV produced a proportion of this bond energy of less than 1%.

Practical Example Plasma Polymer B8

For this Example, polyurethane (PU) was provided with a hydrophilic plasma coating approximately 40 nm thick. The water contact angle was approximately 0°. The coating parameters are shown in Table 10. The bacterial adhesion was determined by the adhesion assay according to ISO 17025.

TABLE 10

Coating parameters of Practical Example plasma polymer B8

|  | Fine cleaning | Coating | Activation |
| --- | --- | --- | --- |
| $O_2$-Flow/sccm | 60 | 400 | 100 |
| HMDSO-Flow/sccm | 0 | 2.5 | 0 |
| Plasma power/W | 800 | 2500 | 1000 |
| Treatment time/min | 10 | 4 | 10 |
| Process pressure/mbar | 0.022 | 0.045 | 0.032 |

Practical Example Plasma Polymer B9

For this example, polyurethane (PU) was provided with a hydrophobic plasma coating approximately 220 nm thick. The water contact angle was approximately 110°. The coating parameters are shown in Table 11. The bacterial adhesion was determined by the adhesion assay according to ISO 17025.

TABLE 11

Coating parameters of Practical Example plasma polymer B9

|  | Fine cleaning | Coating |
|---|---|---|
| $O_2$-Flow/sccm | 60 | 24 |
| HMDSO-Flow/sccm | 0 | 70 |
| Plasma power/W | 800 | 700 |
| Treatment time/min | 10 | 10 |
| Process pressure/mbar | 0.022 | 0.034 |

Example 3

VUV Radiation of an Organosilicon Liquid and a Plasma Polymer

Flat glass substrates (article substrates) were initially coated on one side, as described in Example 1, with biocompatibility layer plasma polymer A1. They were then provided with 270 nm of liquid polydimethylsiloxane silicone oil AK50® (Wacker). In so doing, the silicone oil was applied by an aerosol as a pure substance. Thereafter, for masking purposes, half of the glass substrates was covered by a 2 mm thick glass pane and the other half of the samples was crosslinked under a nitrogen atmosphere at 1 bar by VUV radiation of wavelength 172 nm. For this purpose, the entire sample was irradiated for 6 minutes at a distance of 10 mm from an excimer lamp (manufacturer: Radium Lampenwerk GmbH, Xeradex radiators, 172 nm) with a radiant power density of approximately 0.08 W/cm². In the following, the unmasked half of the sample will be called biocompatibility layer excimer C1.

The uncrosslinked silicone oil under the masking pane could easily be rinsed with isopropanol, so that biocompatibility layer plasma polymer A1 could again be exposed on this surface.

Analogously to biocompatibility layer excimer C1, the silicone oil AK50® was applied to a plurality of glass substrates (article substrates) in an average layer thickness of 360 nm by an aerosol process. A sample was irradiated under a nitrogen atmosphere and at a process pressure of 1 bar at a distance of 10 mm from the lamp and with a radiant power density of approximately 0.08 W/cm² 900 s (Xeradex radiator, 172 nm). Thus, the radiation energy was approximately 75 J/cm². The layer shrunk by 40% to 216 nm as a result of the VUV treatment. In the following, this treatment variant will be called biocompatibility layer excimer C2.

Furthermore, a second sample was also irradiated under a nitrogen atmosphere and a process pressure of 1 bar at a distance of 30 mm from the lamp and with a radiant power density of approximately 0.05 W/cm² 300 s (Xeradex radiator, 172 nm). The radiation energy was approximately 15 J/cm². The layer shrunk by 25% to 270 nm as a result of the VUV treatment. In the following, this treatment variant will be called biocompatibility layer excimer C3.

In addition, a glass pane with the coating plasma polymer A1 was irradiated for 5 minutes at a distance of 10 mm with a radiant power density of approximately 0.08 W/cm² analogously to the silicone oil samples or with a radiation energy of approximately 25 J/cm² (Xeradex radiator, 172 nm). In this case as well, radiation took place under a nitrogen atmosphere and a process pressure of 1 bar. In the following, this treatment variant will be called biocompatibility layer excimer C4.

The results of the XPS measurements of sample C2 treated using an excimer lamp are given in Table 12. Comparative simulations with an additional signal at 288.0 eV produced a proportion of this bond energy of less than 1%.

TABLE 12

| Excimer | Atomic composition (at %) | | | | Ratios | | | Curve Fitting (% of C-total) | | |
|---|---|---|---|---|---|---|---|---|---|---|
|  | N 1s | O 1s | C 1s | Si 2p | C/Si | O/Si | C/O | C | C—O | COO |
| C2 | 0.9 | 65.4 | 6.4 | 27.2 | 0.2 | 2.4 | 0.10 | 66.8 | 18.2 | 15.0 |

Example 4

Biological Assessment of Cell Adhesion

In the following, a test method is described which was used to biologically assess the biocompatibility layers. This is a staining method for cells adhering to surfaces and which is one of the standard methods of cell biology. In this test, the cells which are adhering to or have grown on the surface are directly colored by a stain and are assessed under a microscope. The number of adhering cells can be stated as cells per surface area or as the degree of coverage in percent. Microscopic assessment of the adhering cells also allows the cells to be assessed morphologically. Here, in addition to the number of cells per surface area, an additional assessment can be made as to how the biocompatibility layer acts on the cells. In the case of observing materials which are not transparent, this assessment has to be made using a reflected light microscope (for example the imager M1 microscope by Zeiss).

The cell line V-79 recommended in EN ISO 10993-5: 1999 for testing medical products, inter alia was used for the tests stated below. The hemotoxylin and eosin stain often used in medical histology was used for staining the adherent cells. However, vital stains, for example neutral red can also be used which can also provide information about the vitality of the cells. A distinction can be made between living, damaged and dead cells by the amount of absorbed or incorporated stain. The use of hemotoxylin and eosin for staining cells has the additional advantage that this stain not only colors the cells in visible light but also in the fluorescent range. Consequently, using a fluorescence microscope, it is also possible to make those cells visible which cannot be assessed or can only be poorly assessed by the light-optical microscope due to the quality of the substrate.

The tests were carried out as described in the following. The cell stem culture was prepared in accordance with EN ISO 10993-5: 99. The V79 cells are cultivated in 96×21 mm cell culture dishes, with a growth area of 60.1 cm³ (TPP® Techno Plastic Products AG) at 37° C., 5% $CO_2$ content and a water vapor-saturated atmosphere in an incubator with HAM's F12 medium (10% fetal calf serum [FCS]). With approximately 80% confluence (coverage after 3-4 days), a passage of the cells took place. To prepare a cell suspension, the old medium was firstly suctioned out of the dishes. The dishes were then each washed with 2 ml of phosphate-buffered saline solution (PBS). They were then washed again with 0.5 ml of an undiluted trypsin solution (from pigs' pancreas, SIGMA-Aldrich) and this solution was suctioned off. Thereafter, 3-4 drops of the undiluted trypsin solution were added to the cells and they were incubated for approximately 5 minutes in the incubator. This treatment caused the cells to become detached from the surface and they were visible under the microscope as round cells. To stop the enzymatic reaction, 2 ml of culture medium containing serum were added (HAM's F12).

The cell suspension was thoroughly mixed by careful withdrawal and introduction using a Pasteur pipette. This ensured that even the last cell clusters dissolved. The cells were then determined per ml and the necessary cell number was adjusted for the tests using a Neubauer counting chamber.

The materials to be tested and provided with the biocompatibility coating were transferred into the recesses of a 6-hole cell culture plate (9.6 cm$^2$ growth surface area per recess), the materials having been previously washed with 70% isopropanol, PBS and nutrient medium. 4 ml of cell suspension with 87,500 cells per ml in Ham's F12 medium with 10% serum were then added by pipette per recess. Therefore, a total of 350,000 V79 cells were present per recess. The samples were then incubated at 37° C., 5% CO$_2$ content and under a water vapor-saturated atmosphere for 24 h in an incubator.

After incubation, the nutrient medium was suctioned off and the samples were each washed with 2 ml of PBS on an orbital shaker at 50 rpm for 5 minutes at room temperature. After the last washing step, the surface of each sample was covered with 1 ml of a standard hemotoxylin and eosin solution. After an incubation time of 3 minutes at 50 rpm at room temperature on an orbital shaker, the stain solution is suctioned off and the samples are initially washed for 5 minutes and then for 60 minutes with 2 ml of PBS at 50 rpm at room temperature. The samples were then observed using a reflected light microscope (Zeiss Axio Imager.M1) and digital images (AxioCam MRC by Zeiss) were taken. For substrates which had a very dark surface and thus could only be observed with difficulty under a light-optical microscope, fluorescent images were taken using fluorescent lighting and corresponding filter sets—integral components of the Axio Imager.M1 microscope. The morphology of the adherent cells was evaluated on the one hand to biologically assess the biocompatibility layer. In the case of a surface which promoted cell adhesion, the cells were present in an adherent and elongate form. In the case of coatings with a reduced adhesion, there were either no cells present or cells were present which had a different morphology. On the other hand, the degree of coverage was calculated using image processing software (imageJ). Where there was an increase in the degree of coverage by 40 to 80% compared to the untreated substrate, there was an improved cell adhesion and where there was an increase by more than 80%, there was a significantly improved cell adhesion. In the case of a reduction in the degree of coverage by 40 to 80% compared to the untreated substrate, there was a reduced adhesion and in the case of a reduction by more than 80%, there was a significantly reduced cell adhesion.

TABLE 13

Assessment matrix of cell adhesion with cell line V-79

| Cell adhesion | Change in degree of coverage | Morphology |
|---|---|---|
| improved | Increased by 40% to 80% | Adherent, elongate |
| Significantly improved | Increased by more than 80% | Adherent, elongate |
| reduced | Reduced by 40% to 80% | Spherical-round |
| Significantly reduced | Reduced by more than 80% | Spherical-round |

The results of the tests described in the following using different materials and biocompatibility coatings clearly show that different surface characteristics can be achieved in the materials using the coating. By way of example, some representative results will be discussed in more detail on the basis of FIGS. 9 to 16.

FIG. 9 shows under I. a small aluminum plate, the left-hand side of which was coated with the anti-adhesive biocompatibility layer plasma polymer A1 and the right-hand side was coated with the adhesion-promoting biocompatibility layer plasma polymer B2. For this, plasma polymer A1 was initially applied, then the left half of the sample was covered (masked) by a small stainless steel and then plasma polymer B2 was applied. A detail image of the left-hand side of the sample is shown under II. and a detail image of the right-hand side of the sample is shown under III. The adherent fibroblast cells only grow on the right-hand side. Morphology of the cells shows that they are adherent and elongate. No cells grow on the left-hand surface provided with an anti-adhesive coating.

FIG. 10 shows a substrate made of stainless steel which was coated on the left-hand side with the anti-adhesive biocompatibility layer plasma polymer A1 and on the right-hand side with the adhesion-promoting biocompatibility layer plasma polymer B2. For this, plasma polymer A1 was initially applied, then the left half of the sample was covered (masked) by a small stainless steel plate and then plasma polymer B2 was applied. A detail image of the left-hand side of the sample is shown under II. and a detail image of the right-hand side of the sample is shown under III. The adherent fibroblast cells only grow on the right-hand side. Morphology of the cells shows that they are adherent and elongate. The surface with the coating for reduced cell adhesion shows that here only very few cells can be seen.

FIG. 11 shows a glass substrate which was coated on the left-hand side with the anti-adhesive biocompatibility layer plasma polymer A1 and on the right-hand side with the adhesion-promoting biocompatibility layer plasma polymer B2. For this, plasma polymer A1 was initially applied, then the left half of the sample was covered (masked) by a small stainless steel plate and then plasma polymer B2 was applied. As a result, a direct transition could be realized from plasma polymer A1 to plasma polymer B2, which can be seen in FIG. 11 on the upper photo after the adherent cells had been stained. The adherent fibroblast cells only grow on the right-hand side with the plasma polymer B2, as can be clearly seen in the detail enlargement III. Morphology of the cells shows that they are adherent and elongate. No cells grow on the surface on the left-hand side, plasma polymer A1, as can also be seen in detail enlargement image II.

In FIG. 12, two regions of a glass sample can be seen which were initially coated with the anti-adhesive biocompatibility layer plasma polymer A1. The sample was then covered with silicone oil, one half covered with a glass article substrate and the sample was crosslinked, as described above, to produce the biocompatibility layer excimer C1 using an excimer lamp.

The silicone oil under the article substrate remained uncrosslinked and was wiped with isopropanol. This produced a sample with a locally delimited area with the anti-adhesive biocompatibility layer plasma polymer A1, visible in image II, and a locally delimited area with the biocompatibility layer excimer C1, visible in image I. There is no cell growth on the surface with the exposed anti-adhesive biocompatibility layer plasma polymer A1. On the other hand, there is a significant growth of cells on the surface with biocompatibility layer excimer C1.

FIG. 13 shows ceramics samples, untreated in image I. and provided with the anti-adhesive biocompatibility layer plasma polymer A1 in image II. A reduced number of cells grow on the sample in image II which is provided with the anti-adhesive coating. On the other hand, there is a significant growth of cells on the untreated sample.

FIG. 14 shows PMMA plastics material samples which were provided with different coatings. The upper image I shows the untreated sample in which the cell adhesion is only moderately pronounced. Image III shows the sample provided with the adhesion-promoting biocompatibility plasma polymer B2; here the cells grow in an improved manner. Morphology of the cells shows that they are adherent and elongate. Image II. shows the sample provided with the anti-adhesive biocompatibility layer plasma polymer A1. Here, only a few to no cells grow.

FIG. 15 shows silicone samples, in image I. the untreated reference and in image II. provided with the adhesion-promoting biocompatibility plasma polymer B4. On the sample in image II. which is provided with the adhesion-promoting coating, the cells grow in an improved manner. Morphology of the cells shows that they are adherent and elongate. On the untreated sample in image I., only very few to no cells grow on the surface.

FIG. 16 shows a substrate made of titanium which, on the left-hand side, is untreated (images I and III) and on the right-hand side was provided with the anti-adhesive biocompatibility plasma polymer A1 (images I and II). The cells were observed under a fluorescence microscope to make them visible and the red color image was converted into a grayscale image.

The results of the cell adhesion experiments using cell line V-79 are stated in Table 14.

TABLE 14

Results of cell adhesion experiments using cell line V-79 on different materials and coatings compared to the untreated materials

| Substrate | Coating (From example 1, 2 or 3) | Change in the cell adhesion |
|---|---|---|
| Aluminum | Plasma polymer A1 | Greatly reduced |
| Aluminum | Plasma polymer B2 | Virtually remaining the same (good cell adhesion) |
| Stainless steel | Plasma polymer A1 | Greatly reduced |
| Stainless steel | Plasma polymer B2 | Virtually remaining the same (good cell adhesion) |
| Glass | Plasma polymer A1 | Greatly reduced |
| Glass | Plasma polymer A2 | Greatly reduced |
| Glass | Plasma polymer A3 | Reduced |
| Glass | Plasma polymer A4 | Greatly reduced |
| Glass | Plasma polymer A5 | Greatly reduced |
| Glass | Plasma polymer A6 | Greatly reduced |
| Glass | Plasma polymer B2 | Virtually remaining the same (good cell adhesion) |
| Glass | Plasma polymer B3 | Virtually remaining the same (good cell adhesion) |
| Glass | Excimer C1 | Virtually remaining the same (good cell adhesion) |
| Ceramics | Plasma polymer A1 | Greatly reduced |

TABLE 14-continued

Results of cell adhesion experiments using cell line V-79 on different materials and coatings compared to the untreated materials

| Substrate | Coating (From example 1, 2 or 3) | Change in the cell adhesion |
|---|---|---|
| Ceramics | Plasma polymer B1 | Virtually remaining the same (good cell adhesion) |
| Polymethyl-methacrylate (PMMA) | Plasma polymer A1 | Greatly reduced |
| Polymethyl-methacrylate (PMMA) | Plasma polymer B2 | Improved |
| Silicone | Plasma polymer A1 | Virtually remaining the same (poor cell adhesion) |
| Silicone | Plasma polymer B4 | Greatly improved |
| Titanium | Plasma polymer A1 | Greatly reduced |

Cell adhesion experiments using the cell line L-929 were also carried out analogously to the results of cell adhesion experiments using the cell line V-79. However, in this case, only the cell number was used for the assessment. Since all the experiments were carried out on glass substrates, the assessment criteria stated in Table 15 were established.

TABLE 15

Assessment matrix of cell adhesion using cell line L-929

| Cell adhesion | Change in cell number per surface area compared to glass substrate |
|---|---|
| good | Reduced by less than 45% |
| moderate | Reduced by 45% to 60% |
| reduced | Reduced by 61% to 80% |
| greatly reduced | Reduced by more than 80% |

The results of the cell adhesion experiments using cell line L-929 are stated in Table 16.

TABLE 16

Results of the cell adhesion experiments using cell line L-929 on different materials and coatings compared to the untreated materials

| Substrate | Coating (From Example 1, 2 or 3) | Change in cell adhesion |
|---|---|---|
| Glass | Plasma polymer A1 | greatly reduced |
| Glass | Plasma polymer A6 | moderate |
| Glass | Plasma polymer B1 | good |
| Glass | Plasma polymer U1 | moderate |
| Glass | Plasma polymer U2 | good |
| Glass | Excimer C2 | good |
| Glass | Excimer C3 | moderate |
| Glass | Excimer C4 | reduced |

Biological Assessment of the Bacterial Adhesion

Table 17 shows the relative bacterial adhesion of biocompatibility layer B8, based on uncoated polyurethane (PU) with 100% adhesion according to definition. By rendering the surface hydrophilic (plasma polymer B8), the adhesion of gram-negative *E. Coli* can be reduced to 66%. At the same time, even the adhesion of gram-positive *Staphylococcus epidermidis* decreases. Using the hydrophilic coating, it is possible for the adhesion to be reduced in the case of both types of bacteria.

TABLE 17

Relative change in bacterial adhesion

|  | Escherichia coli | Staphylococcus epidermidis |
|---|---|---|
| PU | 100% | 100% |
| PU + Coating B8 | 66% | 83% |

Table 18 shows the relative bacterial adhesion of biocompatibility layer B9, based on uncoated PU with 100% adhesion according to definition. By rendering the surface hydrophobic (plasma polymer C6), the adhesion of gram-positive *Staphylococcus epidermidis* can be reduced to 56%. However, the adhesion of *E. Coli* is not substantially reduced.

TABLE 18

Relative change in bacterial adhesion

|  | Escherichia coli | Staphylococcus epidermidis |
|---|---|---|
| PU | 100% | 100% |
| PU + Coating B9 | 92% | 56% |

Example 5

Testing for Genotoxicity in Accordance with DIN EN ISO 10993-3

The biocompatibility layers A1, B1, U1 and U2 were tested for DNA-damaging effects by the comet assay. In this test, the genotype (DNA—deoxyribonucleic acid) of single human cells is separated electrophoretically after the respective cells have been incubated with the test surfaces or test substances. If an effect is present which damages the genotype, a tail of DNA fragments in addition to a head of intact DNA can be observed under the microscope in the cells (thus the name comet assay). The presence of the tail clearly indicates that the substances or surfaces result in so-called strand breaks within the DNA molecules. The many small broken strands form a type of tail in the electrophoretic separation, while the intact DNA, conditioned by its original size, is circular.

For testing genotoxicity, the test kit "OxiSelect™" (catalogue number STA-350) manufactured by CELL BIOLABS, San Diego, USA was used (De Boeck et. al [2000], Validation and implementation of an internal standard in Comet assay. Mutat. Res. 469, 181-197).

The human cell line JURKAT was used for the test. An untreated glass surface was used as a negative control. A positive control was carried out with the substance etoposide (glycoside of podophyllotoxin), a chemotherapeutic. The biocompatibility layers A1, B1, U1 and U2, applied to glass bodies, and the negative control (untreated glass surface) were incubated together with the Jurkat cells for 24 hours at 37° C. and 5% $CO_2$ in an incubator. RPMI with 10% serum and an antibacterial penicillin/Streptomycin solution (2%) was used as cell culture medium. Per test, 300,000 cells per mL were applied to the test bodies. A 100 µM solution of etoposide in cell culture medium was used for the positive control. The cells, without a glass substrate, were incubated for 1 hour with the etoposide solution in an incubator (37° C., 5% $CO_2$). The Jurkat cells are so-called suspension cell cultures which, in contrast to the adhering cells, do not grow on the surfaces, but only rest on the surfaces. For the comet assay, the cells were removed and centrifuged at 700×g for 2 minutes and re-suspended in phosphate-buffered saline solution (PBS) and re-centrifuged. Thereafter, the cells were absorbed in a corresponding quantity of PBS buffer, so that a cell concentration of 100,000 cells per milliliter was present in PBS. In the next step, the cells were blended in a ratio of 1:10 with low melting agarose (37° C.), mixed and of this 75 µL were immediately pipetted onto glass substrates (contained in the test kit) and carefully spread out.

In the next step, the glass substrates coated with the cells were treated with cell lysis buffer (14.6 g sodium chloride, 20 mL EDTA solution, 10 mL 10× OxiSelect cell lysis buffer, made up to 100 mL with distilled water—pH 10) and incubated in the dark for 50 minutes at 4° C. Thereafter, the cell lysis buffer is removed and replaced by an alkaline buffer (1.2 g sodium hydroxide, 0.2 mL EDTA solution, made up to 100 mL with distilled water). The cells are then incubated in the dark for a further 30 minutes at 4° C.

For the electrophoretic separation of the DNA or DNA fragments, an alkaline buffer system was used (12.0 g sodium hydroxide, 2 mL EDTA solution, made up to 1 liter with distilled water). For this, the glass substrates coated with the cells were carefully introduced into an electrophoresis chamber and alkaline buffer was poured in until the glass substrates were just covered with buffer. Electrophoresis was carried out for 15 minutes with 300 mA and 25 volts.

The glass substrates with the cells were then washed three times with distilled water. They were then incubated for 5 minutes with 70% ethanol. Thereafter, the ethanol was suctioned off and the glass substrates were dried. To visualize the DNA, the cells were incubated for 15 minutes at room temperature in the agarose on the glass substrate with 100 µL of the fluorescence stain Vista Green DNA. The cells were observed using a fluorescence microscope (Axio Imager M1 from Carl Zeiss Jena, Germany—filter set for excitation 495 nm and emission 517 nm, lens with enlargement×20). For each test, approximately 50 cells were randomly selected and the degree of comet formation was assessed.

The negative control showed that an increased rate of damaged cells could not be observed either due to the glass substrate material used, the incubation conditions and solutions used, or to the cells used or by an erroneously performed comet assay (see in this respect by way of example FIG. 17.*a*). The assessment of the negative control resulted in less than 5% of cells with damage to the DNA.

The positive control made it possible to conclude how a genotoxic substance damages the DNA of the cells and how a tail formation occurs in the comet assay (cf. by way of example FIG. 17.*b*). The treatment of the cells with the substance etoposide produced a marked genotoxic damage of the cells, with more than 95% of the cells having a pronounced comet tail.

To investigate a possible genotoxic effect of the coatings to be used according to the invention, they were also investigated using the comet assay. Assessment of the cells produced less than 5% of cells with a comet tail and the results were thus in the region of the negative control. This result shows that the coatings to be used according to the invention did not have any genotoxic effects in the experiments which were carried out. This result can be applied overall to the layers to be used according to the invention.

Examples of Use

Example of Use 1: Oxygenator Membrane

Polypropylene oxygenator fibers were coated with the hydrophilic plasma polymeric layers B4, B5, B6 and B7. Low-oxygen blood which was in contact with the thus treated fibers could absorb oxygen as efficiently as when the uncoated polypropylene oxygenator fibers were used. By means of blood tests, it was possible to demonstrate that the formation of thrombi was significantly reduced compared to uncoated fibers.

Example of Use 2: Implants

Bone attachment nails are provided with areas with reduced cell attachment (plasma polymeric layer A1), masked as described with respect to FIG. 9, and are then provided with plasma polymeric layer B2. Both areas (A1 and B2) are tested for their biocompatibility, as described in Example 4, and found to be biocompatible. The cell adhesion was low on the surface coated with plasma polymer A1, as described above, whereas the cell adhesion on the surface coated with B2 corresponded to that of stainless steel, as described. Comparable findings result for corresponding coatings of hip, knee, shoulder and spine implants, medical nails, clasps, threads and/or screws. For example, the surfaces inside the joint capsule should be provided with a biocompatibility layer A, while the areas located outside the joint capsule are provided with a biocompatibility layer B.

Example of Use 3: Vessels (Medicament Containers) for Bodily Fluid, Tissue, Biomolecules, Pharmaceuticals Transportation or storage vessels made of glass for dilute aqueous protein solutions can be coated with biocompatibility layer plasma polymer A1 (according to Example 1). This entails a significant reduction in the protein adhesion. Consequently, on the one hand the necessary starting concentration of the proteins can be significantly reduced. On the other hand, the variations in the actual protein concentration are reduced. The proteins are therapeutically effective antibodies.

Example of Use 4: Wound Dressings

Wound dressings were bonded to a supporting polymeric film which is wound from one roll to another in a web fabric process inside the plasma reactor. In so doing, the biocompatibility layer plasma polymer A1 (according to Example 1) was applied. The layer thickness on reference substrates was established at approximately 50 nm. As a result of this plasma coating, the adhesion of the dressing is reduced by cells which are newly formed during the closure of the wound, while an exchange of gas and liquid is ensured.

Example of Use 5: Catheters (Bladder Catheters, Coronary Catheters)

Catheters are coated in the region of their outer surfaces in a plasma reactor. For this, the catheters are coated in a low pressure plasma process. The use of a biocompatibility plasma polymer A1 improves the insertion and withdrawal of the catheters due to the altered surface characteristics.

Long-Term Effect

When the biocompatibility layer plasma polymer B2 (according to Example 1) is used, the coating ensures that the catheter can be joined more effectively to the tissue. Consequently, this means, for example, that a long-term catheter will not slip so easily.

Furthermore, insulin catheters made of stainless steel were provided with biocompatibility plasma polymer A1. This can reduce the amount of cells growing over the insulin catheter and thus the operational life of the catheter can be extended. The coatings also increase the hemocompatibility.

Example of Use 6: Angioplasty Balloon

The use of a biocompatibility plasma polymer A1 (according to Example 1) can facilitate the insertion and withdrawal of the angioplasty balloon due to the altered surface characteristics because the friction can be reduced due to the altered surface tension. This protects the vessel areas which are affected during this intervention.

Example of Use 7: Blood Vessel Stents

Blood vessel stents can firstly be provided with biocompatibility layer plasma polymer A1 (according to Example 1). The outside can then be superficially oxidized by UV radiation. For this, the stents are exposed to an excimer lamp (Xeradex radiator, 172 nm, Radium Lampenwerk GmbG) with light of wavelength 172 nm on a rotating mandrel at a distance of 10 mm under a nitrogen atmosphere at a pressure of 1 bar with a moisture content of approximately 1%. Radiation is preferably carried out for 30 seconds with a radiant power density of approximately 0.82 W/cm$^2$.

This treatment significantly reduces the cell adhesion to the inside of the stent, while the outside still allows a good cell adhesion. Due to the improved cell adhesion on the outside, the gap which forms due to the stent dilation can be closed faster because cells/tissue can grow on the material. However, an inner treatment of the surface with a biocompatibility layer of type A1 prevents blood cells or blood constituents from settling in this region and consequently blocking the stent.

Example of Use 8: Cannulas

Cannulas can be provided with biocompatibility plasma polymer A1 (according to Example 1). The treatment with the biocompatibility layer allows the cannulas to be positioned more easily in tissue or vessels and likewise removed more easily therefrom.

Example of Use 9: Injection System

Cannulas can be provided with biocompatibility layer plasma polymer B2 (according to Example 1). The treatment with the biocompatibility layer allows the cells in the passage region through the tissue to settle more effectively on the injection material. Consequently, an improved healing of the wound/closure is achieved. The penetration of pathogenic agents can be greatly reduced as a result.

Example of Use 11: Artificial Organ

Artificial kidneys or hearts, for example, have been used for some time as transplants. A serious problem in this respect is that the body reacts strongly to, for example the plastics material of these transplants. A biocompatibility layer such as plasma polymer B2 can reduce these severe reactions in the body. On the other hand, a biocompatibility layer, for example plasma polymer A1, is able to prevent the function of specific areas of the artificial organs from being adversely affected by undesired cell growth.

Example of Use 12: Pacemakers and a Power Source Thereof

Pacemakers, together with electrodes, wires and housings can initially be provided with a biocompatibility layer, such as plasma polymer A1 (according to Example A1). The electrodes and wires are then superficially oxidized using an oxygen-containing plasma from an atmospheric pressure plasma nozzle, such as the plasma nozzle PFW10 manufactured by PlasmaTreat. To produce a stream of plasma, air for example is passed through the plasma nozzle with a volume flow of approximately 1400 L/h and a pulsed plasma is produced inside the nozzle (pulse duration approximately 50 µs, pulse/pause ratio approximately 1/3) with a frequency of approximately 18 kHz, an electrode voltage of approximately 10 kV and a plasma power of approximately 0.8 kW. For the treatment, a spacing of approximately 10 mm is adjusted between the plasma nozzle and the surface. The treatment is carried out, for example at a relative speed (between surface and nozzle) of 16 m/min.

As a result, the electrodes and wires can be anchored more effectively in the tissue. Furthermore, there is less growth into the housing of tissue surrounding said housing and the biocompatibility, for example of the electrodes is increased.

Example of Use 13: Prostheses (Open Implants, Epitheses)

Prostheses which are completely surrounded by tissue (so-called endoprostheses) are mentioned in Example of use 2 "Implants". In the case of so-called open implants, a part is located in the body tissue, while the other part is located outside. In the passage region through the skin or tissue, a biocompatibility layer of the plasma polymer B2 type enhances the wound closure, because the tissue cells grow on in an improved manner here. This coating also improves the tissue compatibility of the open prostheses. In addition, the coating prevents bacteria passing into the body via the passage areas and causing infections, because these areas have an improved closure between tissue and prosthetic material.

Example of Use 14: Cochlea Implant

In the field of cochlea implants, biocompatibility coatings of the plasma polymer B2 type can assist the thin connecting wires in becoming better attached to the petrous bone. This helps prevent the electrode set from slipping out so easily. In addition, this coating ensures that the implant becomes integrated in an improved manner in the surrounding tissue. Consequently, incompatibilities, inter alia, with the implant material (for example the silicone) can be prevented, which allows a faster healing process and prevents inflammation.

Example of Use 15: Artificial Heart Valve

The coating of the artificial valve surface with a biocompatibility layer plasma polymer A (according to Example 1) can reduce the tendency for thrombi formation.

Example of Use 16: Heart Valve Ring

A coating of the heart valve ring with a biocompatibility layer plasma polymer B2 allows said heart valve ring to be better integrated into the surrounding heart tissue.

Example of Use 17: Intraocular Lens

The coating of an intraocular lens with a plasma polymeric coating of type B2 can increase the biocompatibility, and consequently the in-growth and wettability of the intraocular lens is improved.

Example of Use 19: Blood Preserving Pouch

During the transportation or storage of blood and blood constituents, the blood and blood constituents must be prevented from reacting with the surface of the pouch material since this could cause undesirable reactions. The treatment of the inner pouch material with a biocompatibility layer plasma polymer A1 can reduce such an undesirable reaction.

Example of Use 20: Cell Culture Container

The treatment of cell culture dishes (Petri dishes, 6-, 12-, 24- and 96 hole plates) with a biocompatibility layer of type B2 can ensure that the cells grow more effectively on the surface of the cell culture containers. This has significant advantages for cell biological and cytotoxicity tests.

In tests with blood cells, for example, a biocompatibility layer plasma polymer A1 can prevent an undesired reaction taking place between these cells and the test vessel, for example an undesired immune reaction.

Example of Use 21: Fermenter

In the field of fermenters, a biocompatibility layer of type B2 can be used to improve the growth of surface structures in the fermenter. Thus, as a result, for example cells which form, for example specific proteins and precipitate in the medium surrounding these cells can settle in an improved manner on the fermenter surface materials (honeycombs, lamellae, 3D-structures, inter alia). These cells are protein-producing CHO cells. Consequently, the quantity of formed protein substance can be increased.

Example of Use 26: Sensor

Fewer or no undesired cells or biomolecules will become attached to sensors, provided with a biocompatibility layer plasma polymer A1, in the region of the sensor surface. A settlement of cells in the region of the sensor frequently leads to failure of these measuring instruments. A biocompatibility layer plasma polymer A1 provides a prolonged operational capability of these sensors.

Example of Use 27: Probes

Percutaneous endoscopic gastric probes (or other probes, for example the percutaneous endoscopic jejunostomy probe) are used to provide patients with nutrition and fluids. Leaks can appear in the passage region through the stomach or intestine which result in the stomach/intestine contents pouring into the abdomen, thus entailing life-threatening peritoneal inflammations. Due to a biocompatibility layer of type B2, the stomach/intestinal tissue can become better attached to the probe material and thus leaks can be reduced.

Example of Use 30: Filter Material

The coating of filter material with a biocompatibility layer plasma polymer B2 allows bacterial cells to adhere to said filter material in an improved manner. The adhering cells can be used, for example to filter specific substances such as organic contaminations out of a liquid flowing round these cells or out of gases, or to decompose them. Applications as biofilters are possible as a result.

Example of Use 31: Biocompatible Scaffolds

In the field of in vitro tissue engineering, substrates based on ceramics or polymeric materials are being used to an increasing extent. It is crucially important for these substrates that autologous cells grow on these substrates. This can be facilitated, for example, using biocompatibility layer plasma polymer B2.

Example of Use 32: Artificial Cornea

Damaged or diseased corneas are nowadays often replaced by the transplantation of donor corneas. However, due to the lack of suitable donor corneas and the risk of renewed disease of the implanted corneas, artificial corneas are in great demand.

To allow the edge of the artificial cornea to grow into the eye's own tissue, this edge is coated with biocompatibility layer plasma polymer B2. In addition, the central region of the artificial cornea can be provided with biocompatibility layer plasma polymer A1 to prevent cells from settling here, which would reduce the vision.

Alternatively, the entire artificial cornea is initially provided with biocompatibility layer plasma polymer A1 and then, after masking the central part, the edge is superficially oxidized by a plasma activation or by excimer radiation in the presence of at least traces of oxygen.

To further improve the in-growth of the peripheral region, specific proteins can be applied to the coating according to the invention.

The invention claimed is:

1. A non-genotoxic medical technical article, comprising a surface region of the article with a crosslinked silicon layer containing silicon, O, C, and H, which is produced by plasma polymerization and/or crosslinking of organosilicon liquids by a plasma process and/or UV radiation of a wavelength of less than 250 nm, without using metals of an atomic number of more than 14, said layer having an atomic ratio of oxygen to silicon of 0.75 to 2.2 and an atomic ratio of carbon to silicon of 0.1 to 2.5, measured by XPS, the article being selected from the group consisting of:

a) a membrane, pipe or tube, oxygenator membrane, catheter, angioplasty balloon, stent, cannula, sensor and probe;

b) an implantable article selected from the group consisting of:

medical nails, clasps, threads and screws, bone attachment nails, stents or vessel prostheses, injection systems, catheters, cardiovascular implants, artificial organs, pacemakers and power sources thereof, prostheses, orthopedic implants, artificial joints, sockets and counterparts cooperating therewith, hip or knee prostheses, spine prostheses, cochlea implants, artificial heart valves, heart valve rings, intraocular lenses, artificial corneas, pumps or other devices for releasing substances in the body, and epitheses;

c) a container for receiving and/or transporting bodily fluid, tissue or the constituents thereof of a living being or of biomolecules including peptides, proteins, lipids, carbohydrates, nucleic acids or active substances prepared therewith;

d) an article for the at least partial covering of skin or a mucous membrane of a living being including wounds; and e) an article otherwise in contact with bodily fluid, tissue or the constituents thereof of a living being or with biomolecules, including peptides, proteins, lipids, carbohydrates, nucleic acids or active substances prepared therewith during intended use;

wherein the crosslinked silicon layer has a thickness of 5 nm to 2 µm.

2. The article as claimed in claim 1, characterized in that the article has a region of the silicon layer with
a) a water contact angle of not more than 35°, or
b) a water contact angle of at least 90°.

3. The article as claimed in claim 1, characterized in that the silicon layer consists, apart from hydrogen, to at least 98 atom %, of the elements silicon, carbon and oxygen and preferably of from 0.1% to 2% of nitrogen, measured by XPS.

4. The article as claimed in claim 3, characterized in that the silicon layer has 3-15 atom % of carbon, based on all the elements apart from hydrogen, determined according to XPS.

5. The article according to claim 1, characterized in that the carbon atoms of the silicon layer have a proportion of 5 to 35% of carbon atoms with a bond to one oxygen atom ("C—O carbon"), measured by XPS.

6. The article according to claim 1, characterized in that the carbon atoms of the silicon layer have a proportion of 5 to 20% of carbon atoms with bonds to two oxygen atoms ("COO carbon"), measured by XPS.

7. The article as claimed in claim 1, characterized in that the silicon layer is produced by crosslinking a methylsiloxane precursor, preferably hexamethyldisiloxane, by plasma polymerization, in particular by low pressure or atmospheric pressure plasma polymerization, or by crosslinking a silicone oil without chemically reactive groups under the effect of a plasma or UV radiation of a wavelength of less than 250 nm, in particular excimer radiation.

8. The article as claimed in claim 7, characterized in that after the precursor or silicone oil was crosslinked and the silicon layer was at least partly oxidized, preferably by plasma effect, flame treatment, oxy-fluorination, laser treatment or a treatment with excimer lamps.

9. A process for the production of an article as claimed in claim 1, comprising the steps of:
a) preparing a crosslinked, silicon layer with an atomic ratio of oxygen to silicon of 0.75 to 2.2, and an atomic ratio of carbon to silicon of 0.1 to 2.5, measured by XPS, and
b) oxidizing at least portions of the layer prepared in step a).

10. The process as claimed in claim 9, characterized in that to delimit the area to be oxidized, a mask is used, preferably a detachable self-adhesive mask, more preferably an adhesive tape, or a printed mask and/or a substance which can be at least partially dissolved or dispersed, preferably in water and is preferably removed after step b).

11. A non-genotoxic medical technical article, comprising a surface region of the article with a crosslinked silicon layer consisting of silicon, O, C, and H, which can be produced by plasma polymerization and/or crosslinking of organosilicon liquids by a plasma process and/or UV radiation of a wavelength of less than 250 nm, without using metals of an atomic number of more than 14, having an atomic ratio of oxygen to silicon of 0.75 to 2.2 and an atomic ratio of carbon to silicon of 0.1 to 2.5, measured by XPS, the article being selected from the group consisting of:

a) a membrane, pipe or tube, in particular oxygenator membrane, catheter, angioplasty balloon, stent, cannula, sensor and probe, b) an implantable article selected from the group consisting of:

medical nails, clasps, threads and screws, bone attachment nails, stents or vessel prostheses, injection systems, catheters, cardiovascular implants, artificial organs, pacemakers and power sources thereof, prostheses, orthopedic implants, artificial joints, artificial sockets and counterparts cooperating therewith, hip or knee prostheses, spine prostheses, cochlea implants, artificial heart valves, heart valve rings or intraocular lenses, artificial corneas, pumps or other devices for releasing substances in the body and epitheses, c) a container for receiving and/or transporting bodily fluid, tissue or the constituents thereof of a living being or of biomolecules, preferably peptides, proteins, lipids, carbohydrates, nucleic acids or active substances prepared therewith, d) an article for the at least partial covering of skin or mucous membrane of a living being and preferably of wounds, and e) an article otherwise in contact with bodily fluid, tissue or the constituents thereof of a living being or with biomolecules, preferably peptides, proteins, lipids, carbohydrates, nucleic acids or active substances prepared therewith during intended use;

wherein the crosslinked silicon layer has a thickness of 5 nm to 2 µm.

12. The article of claim 11, characterized in that the carbon atoms of the silicon layer have a proportion of 5 to 35% of carbon atoms with a bond to one oxygen atom ("C—O carbon"), measured by XPS.

13. The article of claim 11, characterized in that the carbon atoms of the silicon layer have a proportion of 5 to 20% of carbon atoms with bonds to two oxygen atoms ("COO carbon") measured by XPS.

14. A non-genotoxic medical technical article comprising a biocompatibility layer with crosslinked silicon containing silicon, O, C, and H, which is produced by plasma polymerization and/or crosslinking of organosilicon liquids by a plasma process and/or UV radiation of a wavelength of less than 250 nm, without using metals of an atomic number of more than 14, the biocompatibility layer having an atomic ratio of oxygen to silicon of 0.85 to 1.8, an atomic ratio of carbon to silicon of 0.8 to 2.8, an atomic ratio of carbon to oxygen of 0.5 to 2.6, and an atomic ratio of hydrogen to carbon of 1.8 to 3.1, measured by XPS;

wherein the article is selected from the group consisting of:
a) a membrane, pipe or tube, oxygenator membrane, catheter, angioplasty balloon, stent, cannula, sensor and probe;
b) an implantable article selected from the group consisting of:

medical nails, clasps, threads and screws, bone attachment nails, stents or vessel prostheses, injection systems, catheters, cardiovascular implants, artificial organs, pacemakers and power sources thereof, prostheses, orthopedic implants, artificial joints, sockets and counterparts cooperating therewith, hip or knee prostheses, spine prostheses, cochlea implants, artificial heart valves, heart valve rings, intraocular lenses, artificial corneas, pumps or other devices for releasing substances in the body, and epitheses;

c) a container for receiving and/or transporting bodily fluid, tissue or the constituents thereof of a living being or of biomolecules including peptides, proteins, lipids, carbohydrates, nucleic acids or active substances prepared therewith;

d) an article for the at least partial covering of skin or a mucous membrane of a living being including wounds; and e) an article otherwise in contact with bodily fluid, tissue or the constituents thereof of a living being or with biomolecules, including peptides, proteins, lipids, carbohydrates, nucleic acids or active substances prepared therewith during intended use; and wherein the biocompatibility layer of the article has a thickness of 5 nm to 2 µm.

15. A non-genotoxic medical technical article comprising a biocompatibility layer with crosslinked silicon containing silicon, O, C, and H, which is produced by plasma polymerization and/or crosslinking of organosilicon liquids by a plasma process and/or UV radiation of a wavelength of less than 250 nm, without using metals of an atomic number of more than 14, the biocompatibility layer having an atomic ratio of oxygen to silicon of 1.8 to 3.0, an atomic ratio of carbon to silicon of 0.1 to 0.5, an atomic ratio of carbon to oxygen of 0.05 to 0.6, and an atomic ratio of hydrogen to carbon of 0.5 to 3.0, measured by XPS;

wherein the article is selected from the group consisting of:

a) a membrane, pipe or tube, oxygenator membrane, catheter, angioplasty balloon, stent, cannula, sensor and probe;

b) an implantable article selected from the group consisting of:

medical nails, clasps, threads and screws, bone attachment nails, stents or vessel prostheses, injection systems, catheters, cardiovascular implants, artificial organs, pacemakers and power sources thereof, prostheses, orthopedic implants, artificial joints, sockets and counterparts cooperating therewith, hip or knee prostheses, spine prostheses, cochlea implants, artificial heart valves, heart valve rings, intraocular lenses, artificial corneas, pumps or other devices for releasing substances in the body, and epitheses;

c) a container for receiving and/or transporting bodily fluid, tissue or the constituents thereof of a living being or of biomolecules including peptides, proteins, lipids, carbohydrates, nucleic acids or active substances prepared therewith;

d) an article for the at least partial covering of skin or a mucous membrane of a living being including wounds; and e) an article otherwise in contact with bodily fluid, tissue or the constituents thereof of a living being or with biomolecules, including peptides, proteins, lipids, carbohydrates, nucleic acids or active substances prepared therewith during intended use;

wherein the article has a region of the biocompatibility layer with a) a water contact angle of not more than 35°, or b) a water contact angle of at least 90°; and wherein the biocompatibility layer of the article has a thickness of 5 nm to 2 µm.

* * * * *